US012605116B2

(12) United States Patent
Misener et al.

(10) Patent No.: US 12,605,116 B2
(45) Date of Patent: Apr. 21, 2026

(54) FIBER OPTIC MEDICAL SYSTEMS AND DEVICES WITH ELECTRICAL TIP

(71) Applicant: Bard Access Systems, Inc., Salt Lake City, UT (US)

(72) Inventors: Anthony K. Misener, Bountiful, UT (US); Steffan Sowards, Salt Lake City, UT (US); William Robert McLaughlin, Bountiful, UT (US)

(73) Assignee: Bard Access Systems, Inc., Salt Lake City, UT (US)

( * ) Notice: Subject to any disclaimer, the term of this patent is extended or adjusted under 35 U.S.C. 154(b) by 943 days.

(21) Appl. No.: 17/717,919

(22) Filed: Apr. 11, 2022

(65) Prior Publication Data

US 2023/0320663 A1     Oct. 12, 2023

(51) Int. Cl.
| | |
|---|---|
| *A61B 5/00* | (2006.01) |
| *A61B 1/07* | (2006.01) |
| *A61B 5/283* | (2021.01) |
| *A61B 1/313* | (2006.01) |

(52) U.S. Cl.
CPC .............. *A61B 5/6852* (2013.01); *A61B 1/07* (2013.01); *A61B 5/283* (2021.01); *A61B 1/3137* (2013.01); *A61B 2562/0209* (2013.01)

(58) Field of Classification Search
CPC ................................................... A61B 5/6852
See application file for complete search history.

(56) References Cited

U.S. PATENT DOCUMENTS

| | | | |
|---|---|---|---|
| 3,493,288 A | 2/1970 | Oltman et al. | |
| 4,768,855 A | 9/1988 | Nishi et al. | |
| 4,777,955 A | 10/1988 | Brayton et al. | |
| 4,813,429 A | 3/1989 | Eshel et al. | |
| 4,898,176 A | 2/1990 | Petre | |
| 5,099,845 A | 3/1992 | Besz et al. | |
| 5,163,935 A | 11/1992 | Black et al. | |

(Continued)

FOREIGN PATENT DOCUMENTS

| | | |
|---|---|---|
| CA | 3025240 A1 | 11/2017 |
| DE | 102016109601 A1 | 11/2017 |

(Continued)

OTHER PUBLICATIONS

PCT/US2021 /059755 filed Nov. 17, 2021 International Search Report and Written Opinion dated Apr. 29, 2022.

(Continued)

*Primary Examiner* — Joseph M Santos Rodriguez

(74) *Attorney, Agent, or Firm* — Rutan & Tucker LLP

(57)     ABSTRACT

Disclosed herein are medical systems and devices that include an elongate probe configured for insertion into a patient, where the elongate probe includes an electrically conductive (EC) medium extending along probe. The EC medium may take several forms, including a conductive cannula, an ionic solution, a flex circuit, wires, or platings. The probe includes a conductive tip for exchanging electrical signals with a patient. The probe includes optical fiber having shape sensing core fibers, illuminating core fibers and imaging core fibers. A console of the system includes logic executed by one or more processors to perform operations that include providing and/or receiving electrical signals to and from the patient. Operations further include shape sensing of the probe, projecting illuminating light, and receiving imaging light.

22 Claims, 10 Drawing Sheets

(56)                     References Cited

U.S. PATENT DOCUMENTS

| | | | |
|---|---|---|---|
| 5,178,153 A | 1/1993 | Einzig |
| 5,207,672 A | 5/1993 | Roth et al. |
| 5,211,165 A | 5/1993 | Dumoulin et al. |
| 5,220,703 A | 6/1993 | Kanayama et al. |
| 5,275,151 A | 1/1994 | Shockey et al. |
| 5,295,212 A | 3/1994 | Morton et al. |
| 5,423,321 A | 6/1995 | Fontenot |
| 5,454,807 A | 10/1995 | Lennox et al. |
| 5,517,997 A | 5/1996 | Fontenot |
| 5,599,492 A | 2/1997 | Engelson |
| 5,622,170 A | 4/1997 | Schulz |
| 5,633,494 A | 5/1997 | Danisch |
| 5,693,043 A | 12/1997 | Kittrell et al. |
| 5,740,808 A | 4/1998 | Panescu et al. |
| 5,827,313 A | 10/1998 | Ream |
| 5,872,879 A | 2/1999 | Hamm |
| 5,873,842 A | 2/1999 | Brennen et al. |
| 5,879,306 A | 3/1999 | Fontenot et al. |
| 5,906,579 A | 5/1999 | Vander Salm et al. |
| 5,957,831 A | 9/1999 | Adair |
| 6,035,229 A | 3/2000 | Silverstein et al. |
| 6,069,698 A | 5/2000 | Ozawa et al. |
| 6,081,741 A | 6/2000 | Hollis |
| 6,178,346 B1 | 1/2001 | Amundson et al. |
| 6,208,887 B1 | 3/2001 | Clarke |
| 6,210,362 B1 | 4/2001 | Ponzi |
| 6,319,227 B1 | 11/2001 | Mansouri-Ruiz |
| 6,343,227 B1 | 1/2002 | Crowley |
| 6,398,721 B1 | 6/2002 | Nakamura et al. |
| 6,485,482 B1 | 11/2002 | Belef |
| 6,563,105 B2 | 5/2003 | Seibel et al. |
| 6,564,089 B2 | 5/2003 | Izatt et al. |
| 6,593,884 B1 | 7/2003 | Gilboa et al. |
| 6,597,941 B2 | 7/2003 | Fontenot et al. |
| 6,619,857 B2 | 9/2003 | Miyake |
| 6,650,923 B1 | 11/2003 | Lesh et al. |
| 6,685,666 B1 | 2/2004 | Fontenot |
| 6,687,010 B1 | 2/2004 | Horii et al. |
| 6,690,966 B1 | 2/2004 | Rava et al. |
| 6,701,181 B2 | 3/2004 | Tang et al. |
| 6,711,426 B2 | 3/2004 | Benaron et al. |
| 6,816,743 B2 | 11/2004 | Moreno et al. |
| 6,892,090 B2 | 5/2005 | Verard et al. |
| 6,895,267 B2 | 5/2005 | Panescu et al. |
| 6,975,803 B2 | 12/2005 | Koide et al. |
| 7,043,287 B1 | 5/2006 | Khalil et al. |
| 7,132,645 B2 | 11/2006 | Korn |
| 7,273,056 B2 | 9/2007 | Wilson et al. |
| 7,344,533 B2 | 3/2008 | Pearson et al. |
| 7,366,562 B2 | 4/2008 | Dukesherer et al. |
| 7,366,563 B2 | 4/2008 | Kleen et al. |
| 7,396,354 B2 | 7/2008 | Rychnovsky et al. |
| 7,406,346 B2 | 7/2008 | Kleen et al. |
| 7,515,265 B2 | 4/2009 | Alfano et al. |
| 7,532,920 B1 | 5/2009 | Ainsworth et al. |
| 7,587,236 B2 | 9/2009 | Demos et al. |
| 7,603,166 B2 | 10/2009 | Casscells, III et al. |
| 7,699,855 B2 | 4/2010 | Anderson et al. |
| 7,729,735 B1 | 6/2010 | Burchman |
| 7,757,695 B2 | 7/2010 | Wilson et al. |
| 7,758,499 B2 | 7/2010 | Adler |
| 7,840,253 B2 | 11/2010 | Tremblay et al. |
| 7,992,573 B2 | 8/2011 | Wilson et al. |
| 8,032,200 B2 | 10/2011 | Tearney et al. |
| 8,054,469 B2 | 11/2011 | Nakabayashi et al. |
| 8,060,187 B2 | 11/2011 | Marshik-Geurts et al. |
| 8,073,517 B1 | 12/2011 | Burchman |
| 8,078,261 B2 | 12/2011 | Imam |
| 8,182,433 B2 | 5/2012 | Leo et al. |
| 8,187,189 B2 | 5/2012 | Jung et al. |
| 8,197,494 B2 | 6/2012 | Jaggi et al. |
| 8,267,932 B2 | 9/2012 | Baxter et al. |
| 8,369,932 B2 | 2/2013 | Cinbis et al. |
| 8,388,541 B2 | 3/2013 | Messerly et al. |
| 8,571,640 B2 | 10/2013 | Holman |
| 8,597,315 B2 | 12/2013 | Snow et al. |
| 8,622,935 B1 | 1/2014 | Leo |
| 8,700,358 B1 | 4/2014 | Parker, Jr. |
| 8,781,555 B2 | 7/2014 | Burnside et al. |
| 8,798,721 B2 | 8/2014 | Dib |
| 8,968,331 B1 | 3/2015 | Sochor |
| 8,979,871 B2 | 3/2015 | Tyc et al. |
| 9,119,551 B2 | 9/2015 | Qi et al. |
| 9,186,046 B2 | 11/2015 | Ramamurthy et al. |
| 9,339,206 B2 | 5/2016 | Grunwald |
| 9,339,221 B1 | 5/2016 | Heaton, II et al. |
| 9,345,510 B2 | 5/2016 | Patel et al. |
| 9,360,630 B2 | 6/2016 | Jenner et al. |
| 9,549,685 B2 | 1/2017 | Cox et al. |
| 9,560,954 B2 | 2/2017 | Jacobs et al. |
| 9,572,492 B2 | 2/2017 | Simpson et al. |
| 9,622,706 B2 | 4/2017 | Dick et al. |
| 9,645,326 B1 | 5/2017 | Sausse et al. |
| 9,649,048 B2 | 5/2017 | Cox et al. |
| 9,678,275 B1 | 6/2017 | Griffin |
| 9,678,284 B2 | 6/2017 | Coggi et al. |
| 9,737,213 B1 | 8/2017 | Heaton, II et al. |
| 9,872,978 B1 | 1/2018 | Zaborsky et al. |
| 10,231,643 B2 | 3/2019 | Grunwald |
| 10,231,753 B2 | 3/2019 | Burnside et al. |
| 10,258,240 B1 | 4/2019 | Eberle et al. |
| 10,265,133 B1 | 4/2019 | McClellan |
| 10,327,830 B2 | 6/2019 | Grant et al. |
| 10,349,890 B2 | 7/2019 | Misener et al. |
| 10,448,837 B2 | 10/2019 | Manzke et al. |
| 10,492,876 B2 | 12/2019 | Anastassiou et al. |
| 10,551,245 B2 | 2/2020 | Do et al. |
| 10,568,586 B2 | 2/2020 | Begin et al. |
| 10,603,126 B2 | 3/2020 | Karguth et al. |
| 10,620,386 B2 | 4/2020 | Van Der Mark et al. |
| 10,631,718 B2 | 4/2020 | Petroff et al. |
| 10,687,891 B2 | 6/2020 | Belhe et al. |
| 10,932,670 B2 | 3/2021 | Smith et al. |
| 10,939,889 B2 | 3/2021 | Flexman et al. |
| 10,992,078 B2 | 4/2021 | Thompson et al. |
| 10,992,079 B2 | 4/2021 | Stats et al. |
| 11,000,207 B2 | 5/2021 | Burnside et al. |
| 11,000,265 B1 | 5/2021 | Ryu et al. |
| 11,103,321 B2 | 8/2021 | Braun et al. |
| 11,123,047 B2 | 9/2021 | Jaffer et al. |
| 11,259,892 B2 | 3/2022 | Hufford et al. |
| 11,284,916 B2 | 3/2022 | Patel et al. |
| 11,369,342 B2 | 6/2022 | Irisawa |
| 11,382,653 B2 | 7/2022 | Patel et al. |
| 11,474,310 B2 | 10/2022 | Sowards et al. |
| 11,525,670 B2 | 12/2022 | Messerly et al. |
| 11,547,282 B2 | 1/2023 | Weise et al. |
| 11,607,150 B2 | 3/2023 | Schweikert et al. |
| 11,621,518 B2 | 4/2023 | Stats et al. |
| 11,630,009 B2 | 4/2023 | Misener et al. |
| 11,707,205 B2 | 7/2023 | Messerly et al. |
| 11,806,096 B2 | 11/2023 | Flatt et al. |
| 11,850,073 B2 | 12/2023 | Wright et al. |
| 11,931,112 B2 | 3/2024 | Thompson et al. |
| 12,038,338 B2 | 7/2024 | Misener et al. |
| 12,048,478 B2 | 7/2024 | Tegg et al. |
| 12,089,815 B2 | 9/2024 | Sowards et al. |
| 2002/0019627 A1 | 2/2002 | Maguire et al. |
| 2002/0087206 A1 | 7/2002 | Hirschberg et al. |
| 2002/0166190 A1 | 11/2002 | Miyake et al. |
| 2002/0188285 A1 | 12/2002 | Brown |
| 2002/0198457 A1 | 12/2002 | Tearney et al. |
| 2003/0045798 A1 | 3/2003 | Hular et al. |
| 2003/0092995 A1 | 5/2003 | Thompson |
| 2004/0039274 A1 | 2/2004 | Benaron et al. |
| 2004/0111020 A1 | 6/2004 | Long |
| 2004/0111147 A1 | 6/2004 | Rabkin et al. |
| 2004/0242995 A1 | 12/2004 | Maschke |
| 2004/0247268 A1 | 12/2004 | Ishihara et al. |
| 2004/0260182 A1 | 12/2004 | Zuluaga et al. |
| 2005/0033264 A1 | 2/2005 | Redinger |
| 2005/0113719 A1 | 5/2005 | Saadat |
| 2005/0272975 A1 | 12/2005 | McWeeney et al. |
| 2006/0013523 A1 | 1/2006 | Childlers et al. |

(56)                    References Cited

U.S. PATENT DOCUMENTS

| | | |
|---|---|---|
| 2006/0030753 A1 | 2/2006 | Boutillette et al. |
| 2006/0036164 A1 | 2/2006 | Wilson et al. |
| 2006/0069305 A1 | 3/2006 | Couvillon et al. |
| 2006/0100610 A1 | 5/2006 | Wallace et al. |
| 2006/0189959 A1 | 8/2006 | Schneiter |
| 2006/0200049 A1 | 9/2006 | Leo et al. |
| 2006/0241395 A1 | 10/2006 | Kruger et al. |
| 2006/0241492 A1 | 10/2006 | Boese et al. |
| 2007/0060847 A1 | 3/2007 | Leo et al. |
| 2007/0156019 A1 | 7/2007 | Larkin et al. |
| 2007/0179485 A1 | 8/2007 | Yeik et al. |
| 2007/0201793 A1 | 8/2007 | Askins et al. |
| 2007/0225563 A1 | 9/2007 | Ogino |
| 2007/0253673 A1 | 11/2007 | Nielsen et al. |
| 2007/0265503 A1 | 11/2007 | Schlesinger et al. |
| 2007/0287886 A1 | 12/2007 | Saadat |
| 2007/0299425 A1 | 12/2007 | Waner et al. |
| 2008/0034519 A1 | 2/2008 | Fujiwara |
| 2008/0172119 A1 | 7/2008 | Yamasaki et al. |
| 2008/0183128 A1 | 7/2008 | Morriss et al. |
| 2008/0281293 A1 | 11/2008 | Peh et al. |
| 2008/0285909 A1 | 11/2008 | Younge et al. |
| 2009/0005675 A1 | 1/2009 | Grunwald et al. |
| 2009/0018393 A1 | 1/2009 | Dick et al. |
| 2009/0046980 A1 | 2/2009 | Rohlen |
| 2009/0062634 A1 | 3/2009 | Say et al. |
| 2009/0137952 A1 | 5/2009 | Ramamurthy et al. |
| 2009/0208143 A1 | 8/2009 | Yoon et al. |
| 2009/0227992 A1 | 9/2009 | Nir et al. |
| 2009/0234328 A1 | 9/2009 | Cox et al. |
| 2009/0253967 A1 | 10/2009 | Gill et al. |
| 2009/0270729 A1 | 10/2009 | Corbucci et al. |
| 2009/0304582 A1 | 12/2009 | Rousso et al. |
| 2009/0318757 A1 | 12/2009 | Singh |
| 2009/0324161 A1 | 12/2009 | Prisco |
| 2010/0016729 A1 | 1/2010 | Futrell |
| 2010/0030063 A1 | 2/2010 | Lee et al. |
| 2010/0063534 A1 | 3/2010 | Kugler et al. |
| 2010/0114115 A1 | 5/2010 | Schlesinger et al. |
| 2010/0114190 A1 | 5/2010 | Bendett et al. |
| 2010/0139669 A1 | 6/2010 | Piferi et al. |
| 2010/0204569 A1 | 8/2010 | Burnside et al. |
| 2010/0286531 A1 | 11/2010 | Ryan et al. |
| 2010/0292758 A1 | 11/2010 | Lee et al. |
| 2011/0087112 A1 | 4/2011 | Leo et al. |
| 2011/0098533 A1 | 4/2011 | Onoda et al. |
| 2011/0144481 A1 | 6/2011 | Feer et al. |
| 2011/0144630 A1 | 6/2011 | Loeb |
| 2011/0166442 A1 | 7/2011 | Sarvazyan |
| 2011/0172680 A1 | 7/2011 | Younge et al. |
| 2011/0178509 A1 | 7/2011 | Zerfas et al. |
| 2011/0196248 A1 | 8/2011 | Grunwald |
| 2011/0245662 A1 | 10/2011 | Eggers et al. |
| 2011/0295108 A1 | 12/2011 | Cox et al. |
| 2012/0046562 A1 | 2/2012 | Powers et al. |
| 2012/0116161 A1 | 5/2012 | Nieman et al. |
| 2012/0143029 A1 | 6/2012 | Silverstein et al. |
| 2012/0184827 A1 | 7/2012 | Shwartz et al. |
| 2012/0184955 A1 | 7/2012 | Pivotto et al. |
| 2012/0321243 A1 | 12/2012 | Younge et al. |
| 2013/0096482 A1 | 4/2013 | Bertrand et al. |
| 2013/0104884 A1 | 5/2013 | Vazales et al. |
| 2013/0150732 A1 | 6/2013 | Manzke et al. |
| 2013/0188855 A1 | 7/2013 | Desjardins et al. |
| 2013/0190741 A1 | 7/2013 | Moll et al. |
| 2013/0204124 A1 | 8/2013 | Duindam et al. |
| 2013/0211246 A1 | 8/2013 | Parasher |
| 2013/0296652 A1 | 11/2013 | Farr |
| 2013/0296693 A1 | 11/2013 | Wenzel et al. |
| 2013/0310668 A1 | 11/2013 | Young |
| 2013/0324840 A1 | 12/2013 | Zhongping et al. |
| 2014/0031674 A1 | 1/2014 | Newman et al. |
| 2014/0046261 A1 | 2/2014 | Newman et al. |
| 2014/0058368 A1 | 2/2014 | Hogue |
| 2014/0073950 A1 | 3/2014 | Akui et al. |
| 2014/0088413 A1 | 3/2014 | Von Bucsh et al. |
| 2014/0121468 A1 | 5/2014 | Eichenholz |
| 2014/0155948 A1 | 6/2014 | Walsh et al. |
| 2014/0180087 A1 | 6/2014 | Millett et al. |
| 2014/0188133 A1 | 7/2014 | Misener |
| 2014/0221829 A1 | 8/2014 | Maitland et al. |
| 2014/0259477 A1 | 9/2014 | Huang |
| 2014/0268167 A1 | 9/2014 | Friedman et al. |
| 2014/0275997 A1 | 9/2014 | Chopra et al. |
| 2014/0318825 A1 | 10/2014 | Erb et al. |
| 2014/0323887 A1 | 10/2014 | Anderson et al. |
| 2014/0378945 A1 | 12/2014 | Beri |
| 2015/0029511 A1 | 1/2015 | Hooft et al. |
| 2015/0031987 A1 | 1/2015 | Pameijer et al. |
| 2015/0045649 A1 | 2/2015 | O'Dea et al. |
| 2015/0080688 A1 | 3/2015 | Cinbis et al. |
| 2015/0099979 A1 | 4/2015 | Caves et al. |
| 2015/0105654 A1 | 4/2015 | Meyer |
| 2015/0119700 A1 | 4/2015 | Liang et al. |
| 2015/0119724 A1 | 4/2015 | Weber et al. |
| 2015/0209113 A1 | 7/2015 | Burkholz et al. |
| 2015/0209117 A1 | 7/2015 | Flexman et al. |
| 2015/0244465 A1 | 8/2015 | Chou et al. |
| 2015/0270900 A1 | 9/2015 | Hilario et al. |
| 2015/0272445 A1 | 10/2015 | Rozental et al. |
| 2015/0301288 A1 | 10/2015 | Thornton, Jr. |
| 2015/0305816 A1 | 10/2015 | Hadzic |
| 2015/0320977 A1 | 11/2015 | Vitullo et al. |
| 2016/0018602 A1 | 1/2016 | Govari et al. |
| 2016/0151115 A1 | 6/2016 | Karguth et al. |
| 2016/0166326 A1 | 6/2016 | Bakker et al. |
| 2016/0166341 A1 | 6/2016 | Iordachita et al. |
| 2016/0184020 A1 | 6/2016 | Kowalewski et al. |
| 2016/0256228 A1 | 9/2016 | Haartsen et al. |
| 2016/0262627 A1 | 9/2016 | Hecker et al. |
| 2016/0302762 A1 | 10/2016 | Stigall et al. |
| 2016/0331360 A1 | 11/2016 | Hera et al. |
| 2016/0354038 A1 | 12/2016 | Demirtas et al. |
| 2016/0357007 A1 | 12/2016 | Swanson |
| 2016/0374589 A1 | 12/2016 | Misener et al. |
| 2017/0017048 A1 | 1/2017 | Coggi et al. |
| 2017/0020394 A1 | 1/2017 | Harrington |
| 2017/0052091 A1 | 2/2017 | Mori |
| 2017/0079548 A1 | 3/2017 | Silverstein et al. |
| 2017/0082806 A1 | 3/2017 | Van Der Mark et al. |
| 2017/0196479 A1 | 7/2017 | Liu et al. |
| 2017/0201036 A1 | 7/2017 | Cohen et al. |
| 2017/0215973 A1 | 8/2017 | Flexman et al. |
| 2017/0231699 A1 | 8/2017 | Flexman et al. |
| 2017/0273542 A1 | 9/2017 | Au |
| 2017/0273565 A1 | 9/2017 | Ma et al. |
| 2017/0273628 A1 | 9/2017 | Ofek et al. |
| 2017/0290542 A1 | 10/2017 | Chandrasoma |
| 2017/0296037 A1 | 10/2017 | Yoshino |
| 2017/0303824 A1 | 10/2017 | Schlesinger et al. |
| 2017/0311924 A1 | 11/2017 | Sudol |
| 2017/0333136 A1 | 11/2017 | Hladio et al. |
| 2017/0348063 A1 | 12/2017 | Braun et al. |
| 2018/0067268 A1 | 3/2018 | Murakami et al. |
| 2018/0093078 A1 | 4/2018 | Patil et al. |
| 2018/0095231 A1 | 4/2018 | Lowell et al. |
| 2018/0113038 A1 | 4/2018 | Janabi-Sharifi et al. |
| 2018/0116551 A1 | 5/2018 | Newman et al. |
| 2018/0140170 A1 | 5/2018 | Van Putten et al. |
| 2018/0175547 A1 | 6/2018 | Hsu |
| 2018/0239124 A1 | 8/2018 | Naruse et al. |
| 2018/0250088 A1 | 9/2018 | Brennan et al. |
| 2018/0264227 A1 | 9/2018 | Flexman et al. |
| 2018/0289243 A1 | 10/2018 | Landey et al. |
| 2018/0289390 A1 | 10/2018 | Amorizzo et al. |
| 2018/0289927 A1 | 10/2018 | Messerly |
| 2018/0317751 A1 | 11/2018 | Kuboi et al. |
| 2018/0339134 A1 | 11/2018 | Leo |
| 2018/0360545 A1 | 12/2018 | Cole et al. |
| 2018/0369432 A1 | 12/2018 | Zaborsky |
| 2019/0008376 A1 | 1/2019 | Wortelboer et al. |
| 2019/0059743 A1 | 2/2019 | Ramachandran et al. |
| 2019/0110838 A1 | 4/2019 | Martinez et al. |
| 2019/0110839 A1 | 4/2019 | Rafii-Tari et al. |

(56) References Cited

U.S. PATENT DOCUMENTS

| 2019/0110844 A1 | 4/2019 | Misener et al. |
| 2019/0142528 A1 | 5/2019 | Vertikov |
| 2019/0192818 A1 | 6/2019 | Koda et al. |
| 2019/0212761 A1 | 7/2019 | Swanson et al. |
| 2019/0223706 A1 | 7/2019 | Takeuchi et al. |
| 2019/0235182 A1 | 8/2019 | Cheng |
| 2019/0237902 A1 | 8/2019 | Thompson et al. |
| 2019/0271815 A1 | 9/2019 | Van Der Mark et al. |
| 2019/0321110 A1 | 10/2019 | Grunwald et al. |
| 2019/0343424 A1 | 11/2019 | Blumenkranz et al. |
| 2019/0357875 A1 | 11/2019 | Qi et al. |
| 2019/0374196 A1 | 12/2019 | Courtney et al. |
| 2020/0022587 A1 | 1/2020 | Glover et al. |
| 2020/0046434 A1 | 2/2020 | Graetzel et al. |
| 2020/0060718 A1 | 2/2020 | Patel et al. |
| 2020/0069192 A1 | 3/2020 | Sanborn et al. |
| 2020/0093353 A1 | 3/2020 | Tezuka et al. |
| 2020/0155073 A1 | 5/2020 | Hwang et al. |
| 2020/0170724 A1 | 6/2020 | Flatt et al. |
| 2020/0188036 A1 | 6/2020 | Ding et al. |
| 2020/0238051 A1 | 7/2020 | Hwang et al. |
| 2020/0261720 A1 | 8/2020 | Danitz et al. |
| 2020/0275827 A1 | 9/2020 | Weise et al. |
| 2020/0305983 A1 | 10/2020 | Yampolsky et al. |
| 2021/0007796 A1 | 1/2021 | Panescu et al. |
| 2021/0030504 A1 | 2/2021 | Thompson et al. |
| 2021/0045814 A1 | 2/2021 | Thompson et al. |
| 2021/0113274 A1 | 4/2021 | Bydlon et al. |
| 2021/0154440 A1 | 5/2021 | Misener |
| 2021/0156676 A1 | 5/2021 | Messerly et al. |
| 2021/0205585 A1 | 7/2021 | Ullmann et al. |
| 2021/0215871 A1 | 7/2021 | Hayes et al. |
| 2021/0268229 A1 | 9/2021 | Sowards et al. |
| 2021/0271035 A1 | 9/2021 | Sowards et al. |
| 2021/0275256 A1 | 9/2021 | Sowards et al. |
| 2021/0275257 A1 | 9/2021 | Prior et al. |
| 2021/0278604 A1 | 9/2021 | Rohr Daniel et al. |
| 2021/0282867 A1 | 9/2021 | Tegg et al. |
| 2021/0290315 A1 | 9/2021 | Lampert et al. |
| 2021/0298680 A1 | 9/2021 | Sowards et al. |
| 2021/0299879 A1 | 9/2021 | Pinter et al. |
| 2021/0325172 A1 | 10/2021 | Hendriks et al. |
| 2021/0330398 A1 | 10/2021 | Tegg et al. |
| 2021/0389519 A1 | 12/2021 | Choi et al. |
| 2021/0401456 A1 | 12/2021 | Cox et al. |
| 2021/0401509 A1 | 12/2021 | Misener et al. |
| 2021/0402144 A1 | 12/2021 | Messerly |
| 2022/0034733 A1 | 2/2022 | Misener et al. |
| 2022/0039632 A1 | 2/2022 | Polejaev et al. |
| 2022/0039744 A1 | 2/2022 | Koenig |
| 2022/0110695 A1 | 4/2022 | Sowards et al. |
| 2022/0110706 A1 | 4/2022 | Misener et al. |
| 2022/0133401 A1 | 5/2022 | O'Brien et al. |
| 2022/0152349 A1 | 5/2022 | Sowards et al. |
| 2022/0160209 A1 | 5/2022 | Sowards et al. |
| 2022/0188285 A1 | 6/2022 | Ofenloch |
| 2022/0257975 A1 | 8/2022 | Croll et al. |
| 2022/0330891 A1 | 10/2022 | Sowards et al. |
| 2022/0361762 A1 | 11/2022 | Lalancette et al. |
| 2023/0082991 A1 | 3/2023 | Sowards et al. |
| 2023/0149080 A1 | 5/2023 | Wong et al. |
| 2023/0285085 A1 | 9/2023 | Misener et al. |
| 2023/0292997 A1 | 9/2023 | Sowards et al. |
| 2023/0293243 A1 | 9/2023 | Sowards et al. |
| 2023/0338090 A1 | 10/2023 | Misener et al. |
| 2023/0346314 A1 | 11/2023 | Sowards et al. |
| 2023/0346482 A1 | 11/2023 | Sowards et al. |
| 2023/0379057 A1 | 11/2023 | Moore |
| 2023/0414293 A1 | 12/2023 | Farley et al. |
| 2023/0417998 A1 | 12/2023 | Misener et al. |
| 2024/0016425 A1 | 1/2024 | Sowards et al. |
| 2024/0094475 A1 | 3/2024 | Misener et al. |
| 2024/0180470 A1 | 6/2024 | Sowards et al. |
| 2024/0215917 A1 | 7/2024 | Sowards et al. |
| 2024/0423456 A1 | 12/2024 | Sowards et al. |
| 2025/0176853 A1 | 6/2025 | Sowards et al. |
| 2025/0186134 A1 | 6/2025 | Sowards et al. |
| 2025/0249208 A1 | 8/2025 | Sowards et al. |
| 2025/0288366 A1 | 9/2025 | Misener et al. |

FOREIGN PATENT DOCUMENTS

| EP | 2240111 A2 | 10/2010 |
| EP | 2385802 B1 | 8/2013 |
| EP | 3266383 A1 | 1/2018 |
| EP | 2809249 B1 | 12/2018 |
| EP | 3545849 A1 | 10/2019 |
| EP | 3725252 A1 | 10/2020 |
| WO | 99/64099 A1 | 12/1999 |
| WO | 1999064099 A1 | 12/1999 |
| WO | 2006080076 A1 | 8/2006 |
| WO | 2006122001 A2 | 11/2006 |
| WO | 2009/155325 A2 | 12/2009 |
| WO | 2011141830 A1 | 11/2011 |
| WO | 2011150376 A1 | 12/2011 |
| WO | 2012064769 A2 | 5/2012 |
| WO | 2012135339 A1 | 10/2012 |
| WO | 2013114376 A1 | 8/2013 |
| WO | 2014049555 A1 | 4/2014 |
| WO | 2015055413 A1 | 4/2015 |
| WO | 2015074045 A2 | 5/2015 |
| WO | 2016/061431 A1 | 4/2016 |
| WO | 2016193051 A1 | 12/2016 |
| WO | 2018071490 A1 | 4/2018 |
| WO | 2018/096491 A1 | 5/2018 |
| WO | 2019037071 A1 | 2/2019 |
| WO | 2019/046769 A1 | 3/2019 |
| WO | 2019230713 A1 | 12/2019 |
| WO | 2020/142470 A1 | 7/2020 |
| WO | 2021021408 A1 | 2/2021 |
| WO | 2021030092 A1 | 2/2021 |
| WO | 2021108688 A1 | 6/2021 |
| WO | 2021108697 A1 | 6/2021 |
| WO | 2021144317 A1 | 7/2021 |
| WO | 2021178578 A1 | 9/2021 |
| WO | 2022/031613 A1 | 2/2022 |
| WO | 2022/081586 A1 | 4/2022 |
| WO | 2022/081723 A1 | 4/2022 |
| WO | 2022109045 A1 | 5/2022 |
| WO | 2022115624 A1 | 6/2022 |
| WO | 2022221608 A1 | 10/2022 |
| WO | 2023043947 A1 | 3/2023 |
| WO | 2023172652 A1 | 9/2023 |
| WO | 2023177822 A1 | 9/2023 |
| WO | 2023177889 A1 | 9/2023 |
| WO | 2023200734 A1 | 10/2023 |
| WO | 2023205257 A1 | 10/2023 |
| WO | 2023212096 A1 | 11/2023 |
| WO | 2023212098 A1 | 11/2023 |
| WO | 2023249952 A1 | 12/2023 |
| WO | 2024015464 A1 | 1/2024 |
| WO | 2024123837 A1 | 6/2024 |

OTHER PUBLICATIONS

PCT/US2021/019713 filed Feb. 25, 2021 International Search Report and Written Opinion dated Jul. 6, 2021.

PCT/US2021/020079 filed Feb. 26, 2021 International Search Report and Written Opinion dated Jun. 4, 2021.

PCT/US2021/020732 filed Mar. 3, 2021 International Search Report and Written Opinion dated Jul. 5, 2021.

PCT/US2021/060849 filed Nov. 24, 2021 International Search Report and Written Opinion dated Mar. 9, 2022.

U.S. Appl. No. 17/185,777, filed Feb. 25, 2021 Non-Final Office Action dated Feb. 9, 2022.

PCT/US2021/024969 filed Mar. 30, 2021 International Search Report and Written Opinion dated Jul. 19, 2021.

PCT/US2021/054596 filed Oct. 12, 2021 International Search Report and Written Opinion dated Jan. 26, 2022.

U.S. Appl. No. 17/185,777, filed Feb. 25, 2021 Notice of Allowance dated Jun. 10, 2022.

(56) References Cited

OTHER PUBLICATIONS

PCT/US2022/024934 filed Apr. 14, 2022 International Search Report and Written Opinion dated Jul. 18, 2022.
PCT/US2023/020042 filed Apr. 26, 2023 International Search Report and Written Opinion dated Sep. 26, 2023.
PCT/US2023/027527 filed Jul. 12, 2023 International Search Report and Written Opinion dated Oct. 16, 2023.
U.S. Appl. No. 17/187,536, filed Feb. 26, 2021 Advisory Action dated Nov. 21, 2023.
U.S. Appl. No. 17/187,536, filed Feb. 26, 2021 Final Office Action dated Sep. 20, 2023.
U.S. Appl. No. 17/187,536, filed Feb. 26, 2021 Non-Final Office Action dated Dec. 15, 2023.
U.S. Appl. No. 17/217,852, filed Mar. 30, 2021 Notice of Allowance dated Nov. 7, 2023.
U.S. Appl. No. 17/535,406, filed Nov. 24, 2021 Restriction Requirement dated Nov. 24, 2023.
U.S. Appl. No. 17/697,895, filed Mar. 17, 2022 Non-Final Office Action dated Jan. 11, 2024.
U.S. Appl. No. 17/217,852, filed Mar. 30, 2021 Non Final Office Action dated Jun. 7, 2023.
U.S. Appl. No. 17/217,852, filed Mar. 30, 2021 Restriction Requirement dated Mar. 21, 2023.
U.S. Appl. No. 17/697,895, filed Mar. 17, 2022 Non Final Office Action dated Jun. 14, 2023.
PCT/US2023/015416 filed Mar. 16, 2023 International Search Report and Written Opinion dated May 26, 2023.
U.S. Appl. No. 17/187,536, filed Feb. 26, 2021 Non-Final Office Action dated May 17, 2023.
PCT/US2023/019130 filed Apr. 19, 2023 International Preliminary Report on Patentability dated Oct. 8, 2024.
PCT/US2023/020044 filed Apr. 26, 2023 International Preliminary Report on Patentability dated Oct. 29, 2024.
U.S. Appl. No. 17/191,551, filed Mar. 3, 2021 Notice of Allowance dated Nov. 8, 2024.
U.S. Appl. No. 17/689,773, filed Mar. 8, 2022 Advisory Action dated Nov. 1, 2024.
U.S. Appl. No. 17/689,773, filed Mar. 8, 2022 Notice of Allowance dated Jan. 15, 2025.
U.S. Appl. No. 17/696,675, filed Mar. 16, 2022 Advisory Action dated Feb. 6, 2025.
U.S. Appl. No. 17/696,675, filed Mar. 16, 2022 Final Office Action dated Dec. 5, 2024.
U.S. Appl. No. 17/725,394, filed Apr. 20, 2022 Non-Final Office Action dated Nov. 19, 2024.
U.S. Appl. No. 17/731,129, filed Apr. 27, 2022 Restriction Requirement dated Feb. 28, 2025.
U.S. Appl. No. 17/731,155, filed Apr. 27, 2022 Final Office Action dated Jan. 24, 2025.
U.S. Appl. No. 17/849,447, filed Jun. 24, 2022 Non-Final Office Action dated Jan. 17, 2025.
U.S. Appl. No. 17/849,447, filed Jun. 24, 2022 Restriction Requirement dated Apr. 15, 2024.
U.S. Appl. No. 17/863,211, filed Jul. 12, 2022 Non-Final Office Action dated Jan. 29, 2025.
U.S. Appl. No. 17/863,211, filed Jul. 12, 2022 Restriction Requirement dated Nov. 15, 2024.
U.S. Appl. No. 17/945,875, filed Sep. 15, 2022 Non-Final Office Action dated Feb. 27, 2025.
U.S. Appl. No. 18/141,289, filed Apr. 28, 2023 Notice of Allowance dated Jan. 10, 2025.
U.S. Appl. No. 18/607,165, filed Mar. 15, 2024 Non-Final Office Action dated Jan. 15, 2025.
PCT/US2022/043698 filed Sep. 15, 2022 International Search Report and Written Opinion dated Dec. 19, 2022.
U.S. Appl. No. 17/967,794, filed Oct. 17, 2022 Notice of Allowance dated Feb. 15, 2023.
Kirill Bronnikov, Alexey Wolf, Sergey Yakushin, Alexandr Dostovalov, Olga Egorova, Sergey Zhuravlev, Sergey Semjonov, Stefan Wabnitz, and Sergey Babin, "Durable shape sensor based on FBG array inscribed in polyimide-coated multicore optical fiber," Opt. Express 27, 38421-38434 (2019). (Year: 2019).
PCT/US2022/043698 filed Sep. 15, 2022 International Preliminary Report on Patentability dated Mar. 5, 2024.
PCT/US2023/082605 filed Dec. 5, 2023 International Search Report and Written Opinion dated Feb. 28, 2024.
U.S. Appl. No. 17/535,406, filed Nov. 24, 2021 Non-Final Office Action dated Feb. 15, 2024.
U.S. Appl. No. 17/689,773, filed Mar. 8, 2022 Non-Final Office Action dated Mar. 19, 2024.
U.S. Appl. No. 17/731,155, filed Apr. 27, 2022 Restriction Requirement dated Feb. 28, 2024.
U.S. Appl. No. 17/849,447, filed Jun. 24, 2022 Non-Final Office Action dated Apr. 10, 2024.
U.S. Appl. No. 17/187,536, filed Feb. 26, 2021 Final Office Action dated Jul. 2, 2024.
U.S. Appl. No. 17/535,406, filed Nov. 24, 2021 Final Office Action dated Aug. 1, 2024.
U.S. Appl. No. 17/689,773, filed Mar. 8, 2022 Final Office Action dated Aug. 1, 2024.
U.S. Appl. No. 17/696,675, filed Mar. 16, 2022 Non-Final Office Action dated Jun. 11, 2024.
U.S. Appl. No. 17/697,895, filed Mar. 17, 2022 Notice of Allowance dated May 8, 2024.
U.S. Appl. No. 17/725,394, filed Apr. 20, 2022 Non-Final Office Action dated Jun. 17, 2024.
U.S. Appl. No. 18/524,620, filed Nov. 30, 2023 Non-Final Office Action dated Jun. 18, 2024.
PCT/US2023/014849 filed Mar. 8, 2023 International Search Report and Written Opinion dated Jun. 7, 2023.
PCT/US2023/015536 filed Mar. 17, 2023 International Search Report and Written Opinion dated Jun. 22, 2023.
PCT/US2023/018076 filed Apr. 10, 2023 International Search Report and Written Opinion dated Jul. 11, 2023.
PCT/US2023/019130 filed Apr. 19, 2023 International Search Report and Written Opinion dated Jul. 19, 2023.
PCT/US2023/020044 filed Apr. 26, 2023 International Search Report and Written Opinion dated Jul. 19, 2023.
PCT/US2023/025757 filed Jun. 20, 2023 International Search Report and Written Opinion dated Sep. 11, 2023.
U.S. Appl. No. 17/217,852, filed Mar. 30, 2021 Ex Parte Quayle Action dated Sep. 8, 2023.
U.S. Appl. No. 17/499,644, filed Oct. 12, 2021 Notice of Allowance dated Sep. 18, 2023.
U.S. Appl. No. 17/499,644, filed Oct. 12, 2021 Restriction Requirement dated Jul. 11, 2023.
U.S. Appl. No. 17/697,895, filed Mar. 17, 2022 Advisory Action dated Sep. 8, 2023.
U.S. Appl. No. 17/697,895, filed Mar. 17, 2022 Final Office Action dated Aug. 16, 2023.
U.S. Appl. No. 17/529,022, filed Nov. 17, 2021 Notice of Allowance dated Jan. 2, 2025.
U.S. Appl. No. 17/529,022, filed Nov. 17, 2021 Restriction Requirement dated May 2, 2024.
U.S. Appl. No. 17/721,333, filed Apr. 14, 2022 Restriction Requirement dated May 6, 2025.
U.S. Appl. No. 17/725,394, filed Apr. 20, 2022 Advisory Action dated Jun. 5, 2025.
U.S. Appl. No. 17/725,394, filed Apr. 20, 2022 Final Office Action dated Mar. 27, 2025.
U.S. Appl. No. 17/731,129, filed Apr. 27, 2022 Non-Final Office Action dated Apr. 28, 2025.
U.S. Appl. No. 17/731,155, filed Apr. 27, 2022 Advisory Action dated Apr. 3, 2025.
U.S. Appl. No. 17/849,447, filed Jun. 24, 2022 Final Office Action dated May 7, 2025.
U.S. Appl. No. 17/863,211, filed Jul. 12, 2022 Final Office Action dated Jun. 3, 2025.
U.S. Appl. No. 18/075,280, filed Dec. 5, 2022 Non-Final Office Action dated Jun. 11, 2025.
U.S. Appl. No. 18/075,280, filed Dec. 5, 2022 Restriction Requirement dated Mar. 28, 2025.

(56)　　　　　References Cited

OTHER PUBLICATIONS

U.S. Appl. No. 18/607,165, filed Mar. 15, 2024 Notice of Allowance dated Apr. 3, 2025.
PCT/US2023/015536 filed Mar. 17, 2023 International Preliminary Report on Patentability dated Sep. 10, 2024.
PCT/US2023/018076 filed Apr. 10, 2023 International Preliminary Report on Patentability dated Oct. 8, 2024.
U.S. Appl. No. 17/187,536, filed Feb. 26, 2021 Advisory Action dated Oct. 9, 2024.
U.S. Appl. No. 17/187,536, filed Feb. 26, 2021 Notice of Allowance dated Oct. 29, 2024.
U.S. Appl. No. 17/191,551, filed Mar. 3, 2021 Non-Final Office Action dated Aug. 16, 2024.
U.S. Appl. No. 17/529,022, filed Nov. 17, 2021 Non-Final Office Action dated Sep. 30, 2024.
U.S. Appl. No. 17/535,406, filed Nov. 24, 2021 Notice of Allowance dated Oct. 23, 2024.
U.S. Appl. No. 17/731,155, filed Apr. 27, 2022 Non-Final Office Action dated Aug. 22, 2024.
U.S. Appl. No. 17/849,447, filed Jun. 24, 2022 Advisory Action dated Oct. 24, 2024.
U.S. Appl. No. 17/849,447, filed Jun. 24, 2022 Final Office Action dated Aug. 8, 2024.
U.S. Appl. No. 18/141,289, filed Apr. 28, 2023 Non-Final Office Action dated Sep. 28, 2024.
U.S. Appl. No. 18/524,620, filed Nov. 30, 2023 Notice of Allowance dated Sep. 12, 2024.
U.S. Appl. No. 17/696,675, filed Mar. 16, 2022 Notice of Allowance dated Jun. 17, 2025.
U.S. Appl. No. 17/725,394, filed Apr. 20, 2022 Non-Final Office Action dated Jun. 25, 2025.
U.S. Appl. No. 17/731,129, filed Apr. 27, 2022 Final Office Action dated Aug. 27, 2025.
U.S. Appl. No. 17/731,155, filed Apr. 27, 2022 Non-Final Office Action dated Jul. 15, 2025.
U.S. Appl. No. 17/849,447, filed Jun. 24, 2022 Ex Parte Quayle Action dated Sep. 4, 2025.
U.S. Appl. No. 17/863,211, filed Jul. 12, 2022 Advisory Action dated Sep. 11, 2025.
U.S. Appl. No. 17/945,875, filed Sep. 15, 2022 Notice of Allowance dated Jul. 21, 2025.
U.S. Appl. No. 17/721,333, filed Apr. 14, 2022 Non-Final Office Action dated Oct. 16, 2025.
U.S. Appl. No. 17/725,394, filed Apr. 20, 2022 Final Office Action dated Nov. 19, 2025.
U.S. Appl. No. 17/731,129, filed Apr. 27, 2022 Advisory Action dated Oct. 30, 2025.
U.S. Appl. No. 17/849,447, filed Jun. 24, 2022 Notice of Allowance dated Nov. 19, 2025.
U.S. Appl. No. 17/863,211, filed Jul. 12, 2022 Notice of Allowance dated Oct. 22, 2025.
U.S. Appl. No. 18/075,280, filed Dec. 5, 2022 Final Office Action dated Nov. 19, 2025.

*100*

FIBER OPTIC MEDICAL SYSTEMS AND DEVICES WITH ELECTRICAL TIP

BACKGROUND

Elongate medical devices configured for insertion with a patient may be utilized to perform a myriad of treatments and diagnoses. Some devices may also include fiber optic capability. Some medical devices include electrical conducting members extending along the length of the medical device which are often subject to interference.

Disclosed herein are medical devices and systems that include fiber optic capability and electrical capability that address the forgoing.

SUMMARY

Briefly summarized, disclosed herein is a medical device. According to some embodiments, the medical device includes an elongate probe configured for insertion into a patient body, where the elongate probe defines a proximal end and a distal end. The device further includes an optical fiber extending along the elongate probe from the proximal end to the distal end and an electrically conductive (EC) medium extending along the probe from the proximal end to a conductive tip at the distal end.

In some embodiments, the probe includes a cannula formed of a conductive material, where the cannula extends between the proximal end and a distal end, where the optical fiber is disposed within the lumen, and where the cannula defines the EC medium.

In some embodiments, 2 the cannula defines a lumen extending along the cannula, and the optical fiber is disposed within the lumen.

In some embodiments, the cannula defines a closed distal end, and in some embodiments, the closed distal end of the cannula is formed via a welding process.

In some embodiments, the cannula includes a conductive epoxy disposed within the lumen, and the conductive epoxy extends between the proximal end and the distal end.

In some embodiments, the conductive tip includes a conductive tip member, and the cannula surrounds at least a portion of the conductive tip member. In some embodiments, the conductive tip member includes a conductive epoxy.

In some embodiments, the conductive tip member is formed of a non-conductive material, and conductive tip member includes a conductive coating applied to the non-conductive material. In some embodiments, the non-conductive material includes a ceramic material.

In some embodiments, the probe includes a cannula formed of a non-conductive material, where the cannula extending between the proximal end and the distal end. The cannula defines a lumen extending along the cannula, and the optical fiber is disposed with the lumen.

In some embodiments, the cannula includes a conductive substance disposed within the lumen, where the conductive substance extends between the proximal end and the distal end, and where the conductive substance defines the EC medium. In some embodiments, the conductive substance includes a saline solution.

In some embodiments, the cannula includes a flex circuit disposed within the lumen. The flex circuit includes one or more traces extending between the proximal end and the distal end, and the one or more traces define the EC medium.

In some embodiments, the cannula includes one or more wires disposed within the lumen. The one or more wires extend between the proximal end and the distal end, and the one or more wires define the EC medium. In some embodiments, the one or more wires are embedded within the optical fiber. In some embodiments, the one or more wires are embedded within a wall of the cannula.

In some embodiments, the cannula includes one or more stripes of a conductive material disposed on an outside surface of the cannula. The one or more stripes extending between the proximal end and the distal end, and the one or more stripes define the EC medium.

In some embodiments, the optical fiber includes one or more stripes of a conductive material disposed on an outside surface of the optical fiber. The one or more stripes extending between the proximal end and the distal end, and the one or more stripes define the EC medium.

In some embodiments, the optical fiber includes one or more of core fibers extending along a longitudinal length of the optical fiber, where each of the one or more core fibers includes a plurality of sensors distributed along the longitudinal length, and where each sensor of the plurality of sensors being is configured to (i) reflect a light signal of a different spectral width based on received incident light at proximal end, and (ii) change a characteristic of the reflected light signal based on condition experienced by the optical fiber.

In some embodiments, the optical fiber further includes one or more illuminating core fibers, where each of the one or more illuminating core fibers is configured to receive illuminating light at the proximal end and project the illuminating light away from the distal end.

In some embodiments, the optical fiber further includes one or more imaging core fibers, where each of the one or more imaging core fibers is configured to receive imaging light at the distal end and propagate the imaging light along the optical fiber from the distal end to the proximal end.

Also disclosed herein is a medical system comprising a medical device and a console. The medical device includes an elongate probe configured for insertion into a patient body, and the elongate probe defines a proximal end and a distal end. An optical fiber extends along the elongate probe from the proximal end to the distal end, and an electrically conductive (EC) medium extends along the probe from the proximal end to a conductive tip at the distal end. The console is operatively coupled with the medical device at the proximal end. The console includes one or more processors and a non-transitory computer-readable medium having logic stored thereon. The logic when executed by the one or more processors, causes operations of the system that include providing an electrical signal to the patient and/or receiving an electrical signal from the patient.

In some embodiments, the probe includes a cannula formed of a conductive material, where the cannula extends between the proximal end and a distal end. The optical fiber is disposed within the lumen, and the cannula defines the EC medium.

In some embodiments, the conductive tip includes a conductive tip member, coupled with cannula. In some embodiments, the cannula may surround a portion of the conductive tip member.

In some embodiments, the probe includes a cannula formed of a non-conductive material, where the cannula extends between the proximal end and the distal end. The cannula defines a lumen extending along the cannula, and the optical fiber is disposed with the lumen.

In some embodiments, the cannula includes a saline solution disposed within the lumen, the saline solution extending between the proximal end and the distal end, and the saline solution defines the EC medium.

In some embodiments, the cannula includes a flex circuit disposed within the lumen. The flex circuit includes one or more traces extending between the proximal end and the distal end, and the one or more traces define the EC medium.

In some embodiments, the cannula includes one or more wires disposed within the lumen. The one or more wires extend between the proximal end and the distal end, and the one or more wires define the EC medium.

In some embodiments, the cannula includes one or more stripes of a conductive material disposed on an outside surface of the cannula. The one or more stripes extend between the proximal end and the distal end, and the one or more stripes define the EC medium.

In some embodiments, the optical fiber includes one or more stripes of a conductive material disposed on an outside surface of the optical fiber. The one or more stripes extend between the proximal end and the distal end, and the one or more stripes define the EC medium.

In some embodiments, the optical fiber further includes a number of sensing core fibers extending along the optical fiber, where each of the number of sensing core fibers includes a plurality of sensors distributed along the longitudinal length. Each reflective grating of the plurality of reflective grating is configured to (i) reflect a light signal of a different spectral width based on received incident light at proximal end, and (ii) change a characteristic of the reflected light signal based on a condition experienced by the optical fiber. The operations further include determining a physical state of the elongate probe during insertion of the elongate probe within the patient body, wherein determining includes: (i) providing an incident light signal to the number of sensing core fibers; (ii) receiving reflected light signals of different spectral widths of the incident light by one or more of the plurality of sensors; and (iii) processing the reflected light signals associated with the number of sensing core fibers to determine the physical state.

In some embodiments, the optical fiber further includes one or more illuminating core fibers, where each of the one or more illuminating core fibers is configured to receive an illuminating light from the console at the proximal end and project the illuminating light away from the distal end. The operations further include providing the illuminating light to the illuminating core fibers so as to project the illuminating light distally away from the distal end of the probe.

In some embodiments, the optical fiber further includes one or more imaging core fibers, where each of the one or more imaging core fibers is configured to receive an imaging light at the distal end and propagate the imaging light along the optical fiber from the distal end to the console. The operations further include extracting an image of the patient body from the imaging light and causing the image to be portrayed on a display of the system.

In some embodiments, the operations include receiving the electrical signal from the patient and extracting an ECG signal from the electrical signal.

These and other features of the concepts provided herein will become more apparent to those of skill in the art in view of the accompanying drawings and following description, which disclose particular embodiments of such concepts in greater detail.

BRIEF DESCRIPTION OF THE DRAWINGS

Embodiments of the disclosure are illustrated by way of example and not by way of limitation in the figures of the accompanying drawings, in which like references indicate similar elements and in which.

DETAILED DESCRIPTION

Figure 1:
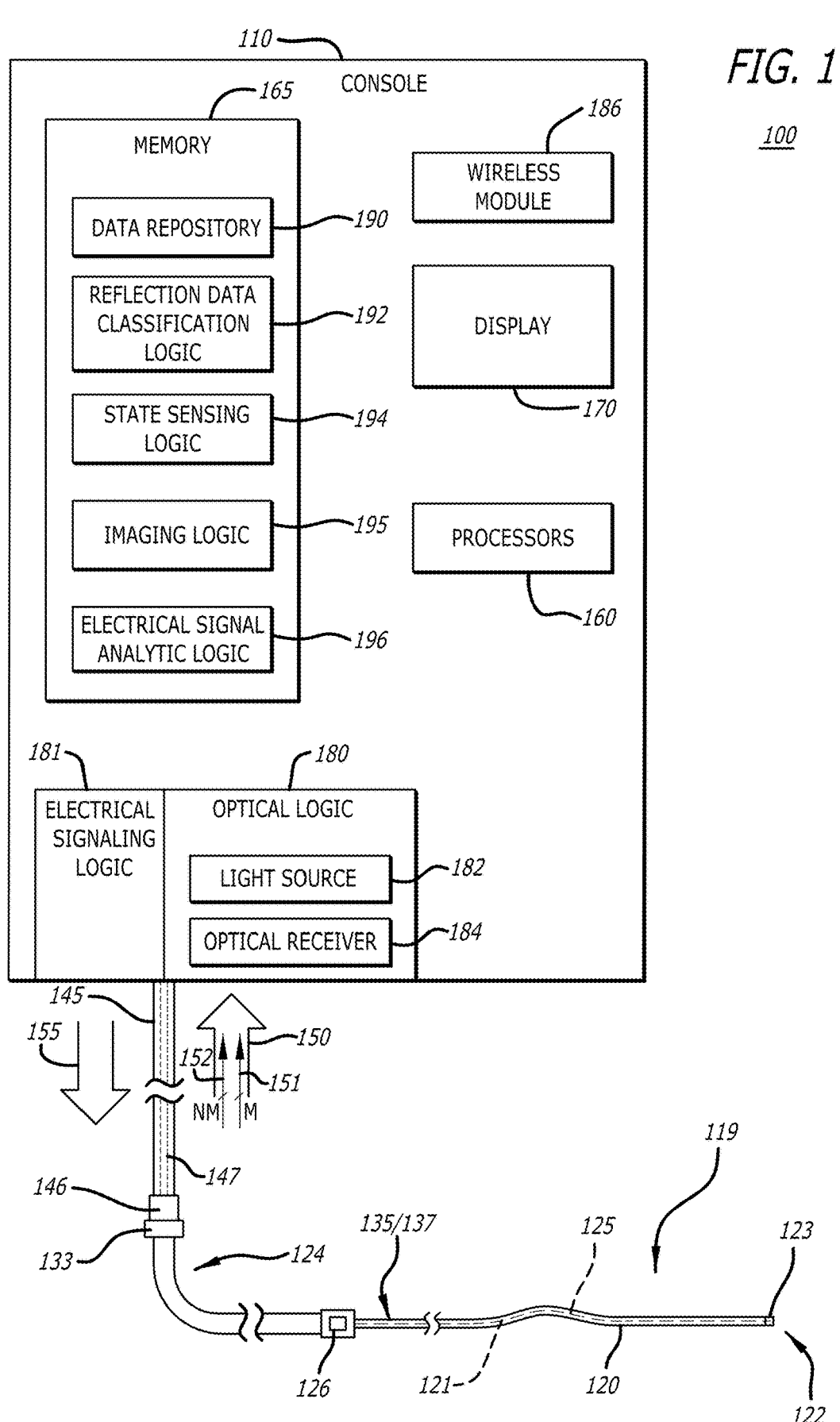
FIG. 1 is an illustrative embodiment of a medical device system including a medical device with fiber optic and electrical capabilities, in accordance with some embodiments.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

With respect to "proximal," a "proximal portion" or a "proximal end portion" of, for example, a probe disclosed herein includes a portion of the probe intended to be near a clinician when the probe is used on a patient. Likewise, a "proximal length" of, for example, the probe includes a length of the probe intended to be near the clinician when the probe is used on the patient. A "proximal end" of, for example, the probe includes an end of the probe intended to be near the clinician when the probe is used on the patient. The proximal portion, the proximal end portion, or the proximal length of the probe can include the proximal end of the probe; however, the proximal portion, the proximal end portion, or the proximal length of the probe need not include the proximal end of the probe. That is, unless context suggests otherwise, the proximal portion, the proximal end portion, or the proximal length of the probe is not a terminal portion or terminal length of the probe.

With respect to "distal," a "distal portion" or a "distal end portion" of, for example, a probe disclosed herein includes a portion of the probe intended to be near or in a patient when the probe is used on the patient. Likewise, a "distal length" of, for example, the probe includes a length of the probe intended to be near or in the patient when the probe is used on the patient. A "distal end" of, for example, the probe includes an end of the probe intended to be near or in the patient when the probe is used on the patient. The distal portion, the distal end portion, or the distal length of the probe can include the distal end of the probe; however, the distal portion, the distal end portion, or the distal length of the probe need not include the distal end of the probe. That is, unless context suggests otherwise, the distal portion, the distal end portion, or the distal length of the probe is not a terminal portion or terminal length of the probe.

The term "logic" may be representative of hardware, firmware or software that is configured to perform one or more functions. As hardware, the term logic may refer to or include circuitry having data processing and/or storage functionality. Examples of such circuitry may include, but are not limited or restricted to a hardware processor (e.g., microprocessor, one or more processor cores, a digital signal processor, a programmable gate array, a microcontroller, an application specific integrated circuit (ASIC), etc.), a semiconductor memory, or combinatorial elements.

Additionally, or in the alternative, the term logic may refer to or include software such as one or more processes, one or more instances, Application Programming Interface(s) (API), subroutine(s), function(s), applet(s), servlet(s), routine(s), source code, object code, shared library/dynamic link library (dll), or even one or more instructions. This software may be stored in any type of a suitable non-transitory storage medium, or transitory storage medium (e.g., electrical, optical, acoustical or other form of propagated signals such as carrier waves, infrared signals, or digital signals). Examples of a non-transitory storage medium may include, but are not limited or restricted to a programmable circuit; non-persistent storage such as volatile memory (e.g., any type of random-access memory "RAM"); or persistent storage such as non-volatile memory (e.g., read-only memory "ROM", power-backed RAM, flash memory, phase-change memory, etc.), a solid-state drive, hard disk drive, an optical disc drive, or a portable memory device. As firmware, the logic may be stored in persistent storage.

The phrases "connected to," "coupled to," and "in communication with" refer to any form of interaction between two or more entities, including but not limited to mechanical, electrical, magnetic, electromagnetic, fluid, and thermal interaction. Two components may be coupled to each other even though they are not in direct contact with each other. For example, two components may be coupled to each other through an intermediate component.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

References to approximations may be made throughout this specification, such as by use of the term "substantially." For each such reference, it is to be understood that, in some embodiments, the value, feature, or characteristic may be specified without approximation. For example, where qualifiers such as "about" and "substantially" are used, these terms include within their scope the qualified words in the absence of their qualifiers. For example, where the term "substantially straight" is recited with respect to a feature, it is understood that in further embodiments, the feature can have a precisely straight configuration.

Reference throughout this specification to "an embodiment" or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

FIG. 1 illustrates an embodiment of a medical instrument placement system including a medical instrument. As shown, the medical instrument placement system (system) 100 generally includes a console 110 and an elongate probe 120 communicatively coupled with the console 110. The elongate probe 120 defines a distal end 122 and includes a console connector 133 at a proximal end 124. The elongate probe 120 includes an optical fiber 135 including multiple core fibers extending along a length of the elongate probe 120 as further described below. The console connector 133 enables the elongate probe 120 to be operably connected to the console 110 via an interconnect 145 including one or more optical fibers 147 (hereinafter, "optical fiber(s)") and an electrically conductive medium 125 extends along the elongate probe 120 from a conductive tip 123 at the distal end 122 to a single optical/electric connector 146 (or dual connectors) at the proximal end 124. Herein, the connector 146 is configured to engage (mate) with the console connector 133 to allow for the propagation of light between the console 110 and the elongate probe 120 as well as the optional propagation of electrical signals from the elongate probe 120 to the console 110. The conductive tip 123 may define an electrode for obtaining electrical signals from the patient.

The elongate probe 120 may be configured to perform any of a variety of medical procedures. As such, the elongate probe 120 may be a component of or employed with a variety of medical instruments/devices 119. In some implementations, the elongate probe 120 may take the form of a guidewire or a stylet, for example. The elongate probe 120 may be formed of a metal, a plastic or a combination thereof.

The elongate probe 120 includes a lumen 121 extending therealong having an optical fiber 135 disposed therein.

In some implementations, the elongate probe 120 may be integrated into a vascular catheter. Other exemplary implementations include drainage catheters, surgery devices, stent insertion and/or removal devices, biopsy devices, endoscopes, and kidney stone removal devices. In short, the elongate probe 120 may be employed with, or the elongate probe 120 may be a component of, any medical device 119 that is inserted into a patient.

According to one embodiment, the console 110 includes one or more processors 160, a memory 165, a display 170, and optical logic 180, although it is appreciated that the console 110 can take one of a variety of forms and may include additional components (e.g., power supplies, ports, interfaces, etc.) that are not directed to aspects of the disclosure. An illustrative example of the console 110 is illustrated in U.S. Pat. No. 10,992,078, the entire contents of which are incorporated by reference herein. The one or more processors 160, with access to the memory 165 (e.g., non-volatile memory or non-transitory, computer-readable medium), are included to control functionality of the console 110 during operation. As shown, the display 170 may be a liquid crystal diode (LCD) display integrated into the console 110 and employed as a user interface to display information to the clinician, especially during an instrument placement procedure. In another embodiment, the display 170 may be separate from the console 110. Although not shown, a user interface is configured to provide user control of the console 110.

According to the illustrated embodiment, the content depicted by the display 170 may change according to which mode the elongate probe 120 is configured to operate: optical, TLS, ECG, or another modality. In TLS mode, the content rendered by the display 170 may constitute a two-dimensional or three-dimensional representation of the physical state (e.g., length, shape, form, and/or orientation) of the elongate probe 120 computed from characteristics of reflected light signals 150 returned to the console 110. The reflected light signals 150 constitute light of a specific spectral width of broadband incident light 155 reflected back to the console 110. According to one embodiment of the disclosure, the reflected light signals 150 may pertain to various discrete portions (e.g., specific spectral widths) of broadband incident light 155 transmitted from and sourced by the optical logic 180, as described below.

According to one embodiment of the disclosure, an activation control 126, included on the elongate probe 120, may be used to set the elongate probe 120 into a desired operating mode and selectively alter operability of the display 170 by the clinician to assist in medical device placement. For example, based on the modality of the elongate probe 120, the display 170 of the console 110 can be employed for optical modality-based guidance during probe advancement through the vasculature or TLS modality to determine the physical state (e.g., length, form, shape, orientation, etc.) of the elongate probe 120. In one embodiment, information from multiple modes, such as optical, TLS or ECG for example, may be displayed concurrently (e.g., at least partially overlapping in time).

Referring still to FIG. 1, the optical logic 180 is configured to support operability of the elongate probe 120 and enable the return of information to the console 110, which may be used to determine the physical state associated with the elongate probe 120 along or an image of the patient body. Electrical signals, such as ECG signaling, may be processed via an electrical signaling logic 181 that supports receipt and processing of the received electrical signals from the elongate probe 120, (e.g., ports, analog-to-digital conversion logic, etc.). Electrical signals, such as a pacemaker signal, for example, may also be defined and provided by the electrical signaling logic 181. The physical state of the elongate probe 120 may be based on changes in characteristics of the reflected light signals 150 received at the console 110 from the elongate probe 120. The characteristics may include shifts in wavelength caused by strain on certain regions of the core fibers integrated within the optical fiber 135 positioned within or operating as the elongate probe 120, as shown below. As discussed herein, the optical fiber 135 may be comprised of core fibers $137_1$-$137_M$ (M=1 for a single core, and M≥2 for a multi-core), where the core fibers $137_1$-$137_M$ may collectively be referred to as core fiber(s) 137. Unless otherwise specified or the instant embodiment requires an alternative interpretation, embodiments discussed herein will refer to an optical fiber 135. From information associated with the reflected light signals 150, the console 110 may determine (through computation or extrapolation of the wavelength shifts) the physical state of the elongate probe 120.

According to one embodiment of the disclosure, as shown in FIG. 1, the optical logic 180 may include a light source 182 and an optical receiver 184. The light source 182 is configured to transmit the incident light 155 (e.g., broadband) for propagation over the optical fiber(s) 147 included in the interconnect 145, which are optically connected to the optical fiber 135 within the elongate probe 120. In one embodiment, the light source 182 is a tunable swept laser, although other suitable light sources can also be employed in addition to a laser, including semi-coherent light sources, LED light sources, etc.

The optical receiver 184 is configured to: (i) receive returned optical signals, namely reflected light signals 150 received from optical fiber-based reflective gratings (sensors) fabricated within each core fiber of the optical fiber 135 deployed within the elongate probe 120, and (ii) translate the reflected light signals 150 into reflection data (from a data repository 190), namely data in the form of electrical signals representative of the reflected light signals including wavelength shifts caused by strain. The reflected light signals 150 associated with different spectral widths may include reflected light signals 151 provided from sensors positioned in the center core fiber (reference) of the optical fiber 135 and reflected light signals 152 provided from sensors positioned in the periphery core fibers of the optical fiber 135, as described below. Herein, the optical receiver 184 may be implemented as a photodetector, such as a positive-intrinsic-negative "PIN" photodiode, avalanche photodiode, or the like.

As shown, both the light source 182 and the optical receiver 184 are operably connected to the one or more processors 160, which governs their operation. Also, the optical receiver 184 is operably coupled to provide the reflection data (from the data repository 190) to the memory 165 for storage and processing by reflection data classification logic 192. The reflection data classification logic 192 may be configured to: (i) identify which core fibers pertain to which of the received reflection data (from the data repository 190) and (ii) segregate the reflection data stored within the data repository 190 provided from reflected light signals 150 pertaining to similar regions of the elongate probe 120 or spectral widths into analysis groups. The reflection data for each analysis group is made available to state sensing logic 194 for analytics.

According to one embodiment of the disclosure, the state sensing logic 194 is configured to compare wavelength shifts measured by sensors deployed in each periphery core fiber at the same measurement region of the elongate probe 120 (or same spectral width) to the wavelength shift at a center core fiber of the optical fiber 135 positioned along central axis and operating as a neutral axis of bending. From these analytics, the state sensing logic 194 may determine the shape the core fibers have taken in three-dimensional space and may further determine the current physical state of the elongate probe 120 in three-dimensional space for rendering on the display 170.

According to one embodiment of the disclosure, the state sensing logic 194 may generate a rendering of the current physical state of the elongate probe 120, based on heuristics or run-time analytics. For example, the state sensing logic 194 may be configured in accordance with machine-learning techniques to access the data repository 190 with pre-stored data (e.g., images, etc.) pertaining to different regions of the elongate probe 120 in which reflected light from core fibers have previously experienced similar or identical wavelength shifts. From the pre-stored data, the current physical state of the elongate probe 120 may be rendered. Alternatively, as another example, the state sensing logic 194 may be configured to determine, during run-time, changes in the physical state of each region of the optical fiber 135 based on at least: (i) resultant wavelength shifts experienced by different core fibers within the optical fiber 135, and (ii) the relationship of these wavelength shifts generated by sensors positioned along different periphery core fibers at the same cross-sectional region of the optical fiber 135 to the wavelength shift generated by a sensor of the center core fiber at the same cross-sectional region. It is contemplated that other processes and procedures may be performed to utilize the wavelength shifts as measured by sensors along each of the core fibers within the optical fiber 135 to render appropriate changes in the physical state of the elongate probe 120, especially to enable guidance of the elongate probe 120 when positioned multi-core within the patient and at a desired destination within the body.

The light source 182 and the optical receiver 184 may also be configured to provide illuminating light to the optical fiber 135 and receive imaging light signals from the optical fiber 135, respectively. The imaging logic 195 may be configured to (i) process imaging light signals, (ii) extract/determine an image from the imaging light signals, and (iii) cause the image to be portrayed on the display 170.

The console 110 may further include optional electrical signaling logic 181 configured to receive one or more electrical signals from the elongate probe 120. The elongate probe 120 is configured to support both optical connectivity as well as electrical connectivity. The electrical signaling logic 181 receives the electrical signals (e.g., ECG signals) from the elongate probe 120 via the conductive medium. The electrical signal logic 196 may process by to extract an ECG signal from the electrical signals. The electrical signal logic 196 may further cause an ECG waveform to be portrayed on the display 170.

It is contemplated that other processes and procedures may be performed to utilize the wavelength shifts as measured by sensors along each of the core fibers within the optical fiber 130 to render appropriate changes in the physical state of the probe 120, especially to enable guidance of the probe 120 when positioned multi-core within the patient and at a desired destination within the body. For example, wavelength shifts as measured by sensors along one or more of the core fibers may be based on physical states or condition of the probe 120 other than or in addition to longitudinal strain experienced by the elongate probe 120. Alternative or additional physical states may include one or more of torsional strain, temperature, motion, oscillations, pressure, or fluid flow adjacent the elongate probe.

Figure 2:
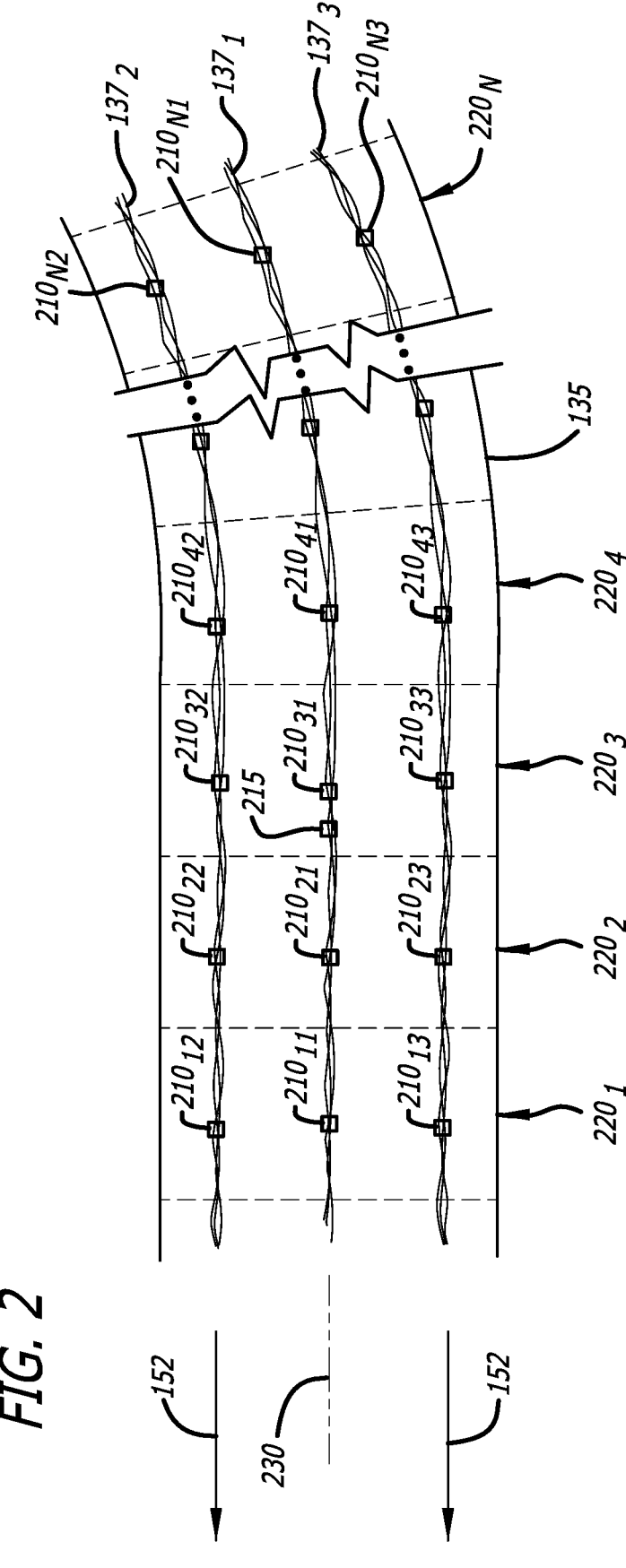
FIG. 2 is an exemplary embodiment of a structure of a section of the multi-core optical fiber included within the elongate probe of FIG. 1, in accordance with some embodiments.

Referring to FIG. 2, an exemplary embodiment of a structure of a section of the multi-core optical fiber of FIG. 1 is shown in accordance with some embodiments. The multi-core optical fiber section 200 of the optical fiber 135 depicts certain core fibers $137_1$-$137_M$ (M≥2, M=4 as shown, see FIG. 3A) along with the spatial relationship between sensors (e.g., reflective gratings) $210_{11}$-$210_{NM}$ (N≥2; M≥2) present within the core fibers $137_1$-$137_M$, respectively. As noted above, the core fibers $137_1$-$137_M$ may be collectively referred to as "the core fibers 137."

As shown, the section 200 is subdivided into a plurality of cross-sectional regions $220_1$-$220_N$, where each cross-sectional region $220_1$-$220_N$ corresponds to reflective gratings $210_{11}$-$210_{14}$ . . . $210_{N1}$-$210_{N4}$. Some or all of the cross-sectional regions $220_1$ . . . $220_N$ may be static (e.g., prescribed length) or may be dynamic (e.g., vary in size among the regions $220_1$ . . . $220_N$). A first core fiber $137_1$ is positioned substantially along a center (neutral) axis 230 while core fiber $137_2$ may be oriented within the cladding of the optical fiber 135, from a cross-sectional, front-facing perspective, to be position on "top" the first core fiber $137_1$. In this deployment, the core fibers $137_3$ and $137_4$ may be positioned "bottom left" and "bottom right" of the first core fiber $137_1$. As examples, FIGS. 3A-4B provides illustrations of such.

Referencing the first core fiber $137_1$ as an illustrative example, when the elongate probe 120 (see FIG. 1) is operative, each of the reflective gratings $210_1$-$210_N$ reflects light for a different spectral width. As shown, each of the gratings $210_{1i}$-$210_{Ni}$ (1≤i≤M) is associated with a different, specific spectral width, which would be represented by different center frequencies of $f_1$ . . . $f_N$, where neighboring spectral widths reflected by neighboring gratings are non-overlapping according to one embodiment of the disclosure.

Herein, positioned in different core fibers $137_2$-$137_3$ but along at the same cross-sectional regions $220$-$220_N$ of the optical fiber 135, the gratings $210_{12}$-$210_{N2}$ and $210_{13}$-$210_{N3}$ are configured to reflect incoming light at same (or substantially similar) center frequency. As a result, the reflected light returns information that allows for a determination of the physical state of the core fibers 137 (and the elongate probe 120) based on wavelength shifts measured from the returned, reflected light. In particular, strain (e.g., compression or tension) applied to the optical fiber 135 (e.g., at least core fibers $137_2$-$137_3$) results in wavelength shifts associated with the returned, reflected light. Based on different locations, the core fibers $137_1$-$137_4$ experience different types and degree of strain based on angular path changes as the elongate probe 120 advances in the patient.

For example, with respect to the multi-core optical fiber section 200 of FIG. 2, in response to angular (e.g., radial) movement of the elongate probe 120 is in the left-veering direction, the fourth core fiber $137_4$ (see FIG. 3A) of the optical fiber 135 with the shortest radius during movement (e.g., core fiber closest to a direction of angular change) would exhibit compression (e.g., forces to shorten length). At the same time, the third core fiber $137_3$ with the longest radius during movement (e.g., core fiber furthest from the direction of angular change) would exhibit tension (e.g., forces to increase length). As these forces are different and unequal, the reflected light from reflective gratings $210_{N2}$ and $210_{N3}$ associated with the core fiber $137_2$ and $137_3$ will exhibit different changes in wavelength. The differences in wavelength shift of the reflected light signals 150 can be used to extrapolate the physical configuration of the elongate probe 120 by determining the degrees of wavelength change caused by compression/tension for each of the periphery fibers (e.g., the second core fiber $137_2$ and the third core fiber $137_3$) in comparison to the wavelength of the reference core fiber (e.g., first core fiber $137_1$) located along the neutral axis 230 of the optical fiber 135. These degrees of wavelength change may be used to extrapolate the physical state of the elongate probe 120. The reflected light signals 150 are reflected back to the console 110 via individual paths over a particular core fiber $137_1$-$137_M$.

In some embodiments, although not required, that the optical fiber 135 may include sensors 215, where wavelength shifts as measured by the sensors 215 along the optical fiber 135 may be based on physical states or conditions of the probe 120 that include one or more than a temperature experienced by the elongate probe 120, a pressure exerted on the elongate probe 120, or a fluid flow (e.g., blood flow) adjacent the elongate probe 120. The sensors 215 may located along any of the core fibers 137 or along additional core fibers (not shown). In accordance with the sensors 215, the state sensing logic 194 may be configured to determine one or more of the temperature, the pressure, or the fluid flow.

Figure 3A:
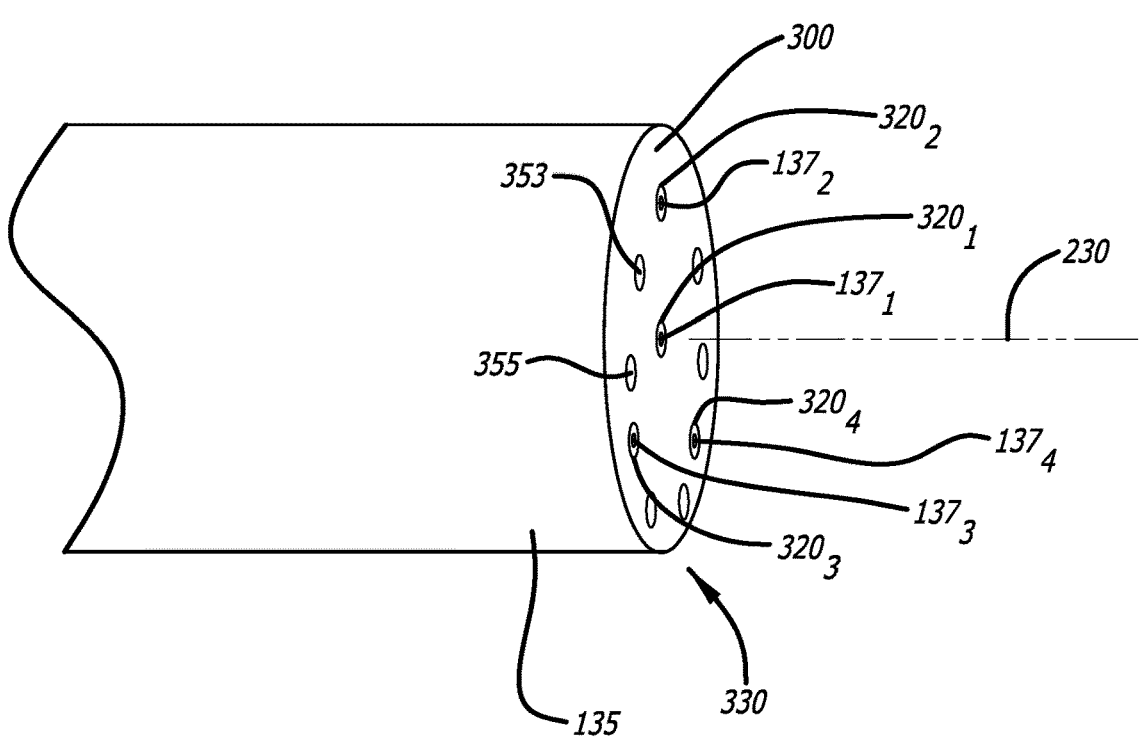
FIG. 3A illustrates an embodiment of the optical fiber of FIG. 1, in accordance with some embodiments.

Referring to FIG. 3A, a first exemplary embodiment of the elongate probe 120 of FIG. 1 supporting both an optical and electrical signaling is shown in accordance with some embodiments. Herein, the elongate probe 120 features a centrally located a multi-core optical fiber 135, which includes a cladding 300 and a plurality of core fibers $137_1$-$137_M$ (M≥2; M=4) residing within a corresponding plurality of lumens $320_1$-$320_M$. While the optical fiber 135 is illustrated within four (4) core fibers $137_1$-$137_4$, a greater number of core fibers $137_1$-$137_M$ (M>4) may be deployed to provide a more detailed three-dimensional sensing of the physical state (e.g., shape, etc.) of the optical fiber 135 and the elongate probe 120 deploying the optical fiber 135.

The optical fiber 135 is encapsulated within a concentric tubing 310 (e.g., braided tubing as shown) positioned over a low coefficient of friction layer 335. The concentric tubing 310, may in some embodiments, feature a "mesh" construction, in which the spacing between the intersecting elements may be selected based on the degree of rigidity/flexibility desired for the elongate probe 120, as a greater spacing may provide a lesser rigidity, and thereby, a more flexible elongate probe 120.

Figure 3B:
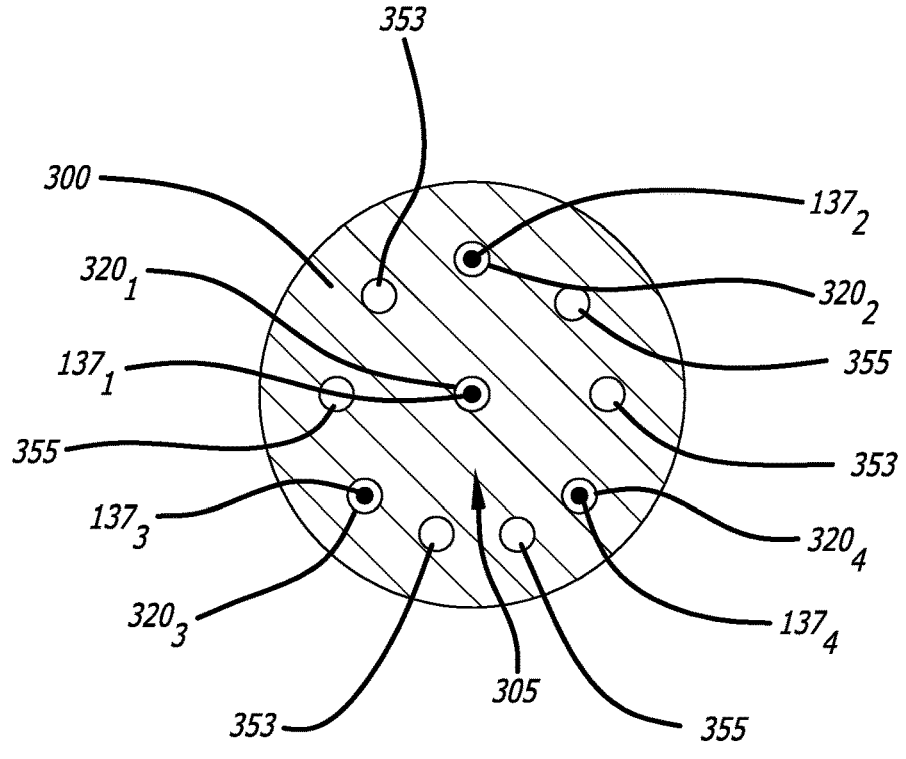
FIG. 3B is a cross sectional view of the optical fiber of FIG. 3A, in accordance with some embodiments.

According to this embodiment of the disclosure, as shown in FIGS. 3A-3B, the core fibers $137_1$-$137_4$ include (i) a central core fiber $137_1$ and (ii) a plurality of periphery core fibers $137_2$-$137_4$, which are maintained within lumens $320_1$-$320_4$ formed in the cladding 300. According to one embodiment of the disclosure, one or more of the lumen $320_1$-$320_4$ may be configured with a diameter sized to be greater than the diameter of the core fibers $137_1$-$137_4$. By avoiding a majority of the surface area of the core fibers $137_1$-$137_4$ from being in direct physical contact with a wall surface of the lumens $320_1$-$320_4$, the wavelength changes to the incident light are caused by angular deviations in the optical fiber 135 thereby reducing influence of compression and tension forces being applied to the walls of the lumens $320_1$-$320_M$, not the core fibers $137_1$-$137_M$ themselves.

As further shown in FIGS. 3A-3B, the core fibers $137_1$-$137_4$ may include central core fiber $137_1$ residing within a first lumen $320_1$ formed along the first neutral axis 230 and a plurality of core fibers $137_2$-$137_4$ residing within lumens $320_2$-$320_4$ each formed within different areas of the cladding 300 radiating from the first neutral axis 230. In general, the core3fibers $137_2$-$137_4$, exclusive of the central core fiber $137_1$, may be positioned at different areas within a cross-sectional area 305 of the cladding 300 to provide sufficient separation to enable three-dimensional sensing of the optical fiber 135 based on changes in wavelength of incident light propagating through the core fibers $137_2$-$137_4$ and reflected back to the console for analysis.

For example, where the cladding 300 features a circular cross-sectional area 305 as shown in FIG. 3B, the core fibers $137_2$-$137_4$ may be positioned substantially equidistant from each other as measured along a perimeter of the cladding 300, such as at "top" (12 o'clock), "bottom-left" (8 o'clock) and "bottom-right" (4 o'clock) locations as shown. Hence, in general terms, the core fibers $137_2$-$137_4$ may be positioned within different segments of the cross-sectional area 305. Where the cross-sectional area 305 of the cladding 300 has a distal tip 330 and features a polygon cross-sectional shape (e.g., triangular, square, rectangular, pentagon, hexagon, octagon, etc.), the central core fiber $137_1$ may be located at or near a center of the polygon shape, while the remaining core fibers $137_2$-$137_M$ may be located proximate to angles between intersecting sides of the polygon shape.

With further reference to FIG. 3B, the elongate probe 120 may optionally include a number of core fibers 353 configured for propagating illuminating light (e.g., the illuminating light 653 of FIG. 6) distally along the elongate probe 120 from the console connector 133 to the distal end 122. The illuminating light may project distally away from the distal end 122 (FIG. 1) of the elongate probe 120 (see FIG. 1) to provide visual illumination to an interior portion of the patient body for the purpose of obtaining an image of the portion of the patient body, e.g., an image of an interior of a vascular lumen of the patient adjacent the distal end of the elongate probe 120.

The elongate probe 120 may further optionally include a number of core fibers 355 configured for propagating imaging light (e.g., the imaging light 655 of FIG. 6) proximally along the elongate probe 120 from the distal end 122 to the console connector 133 (see FIG. 1). The imaging light, as may be defined by the illumination of the patient (e.g., an interior of a vascular lumen of the patient adjacent the distal end of the elongate probe 120), may be received by the core fibers 355 at the distal end 122.

Figure 4A:
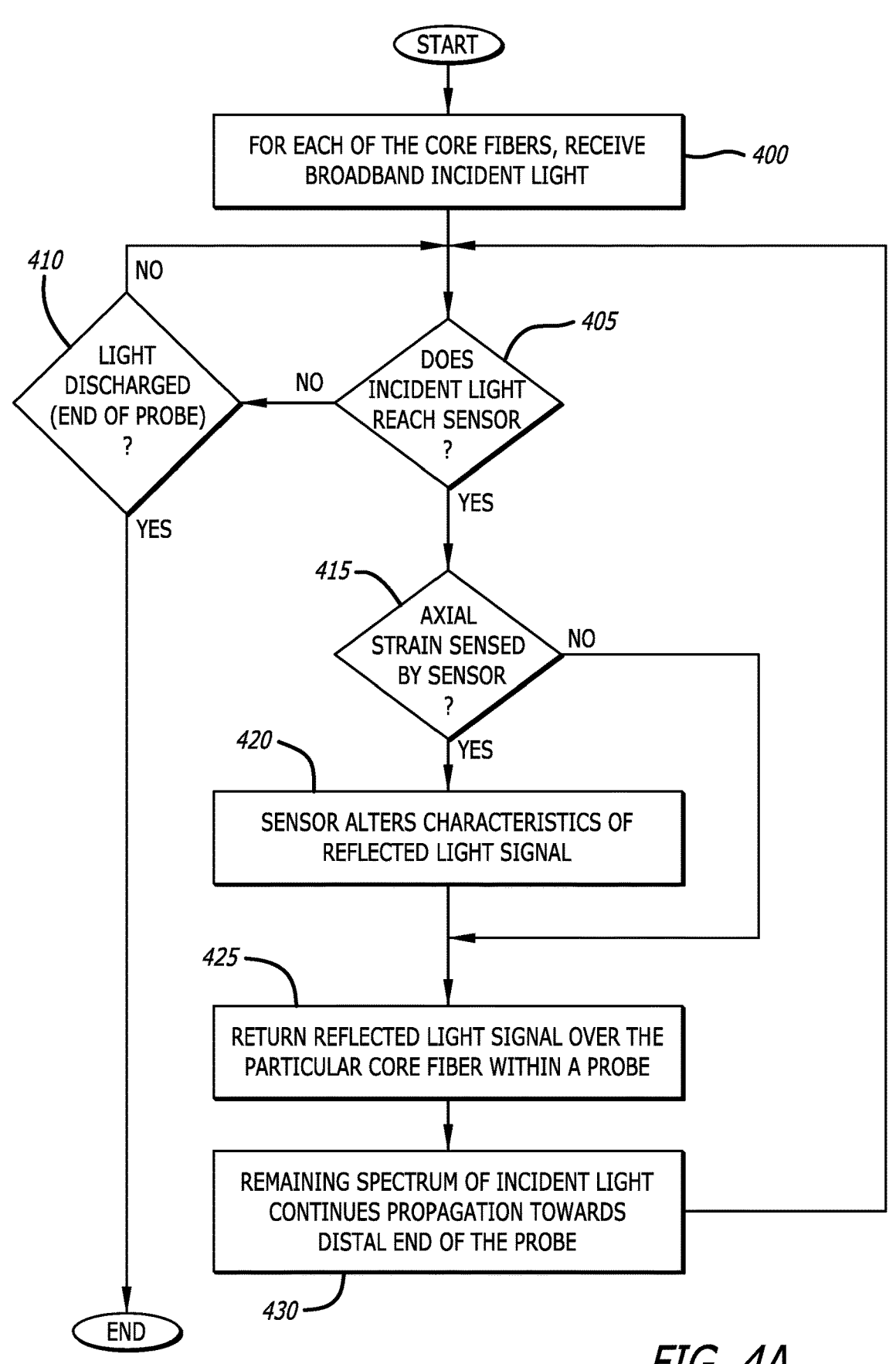
FIGS. 4A-4B are flowcharts of the methods of operations conducted by the medical device system of FIG. 1 to achieve optic three-dimensional shape sensing, in accordance with some embodiments.
Figure 4B:
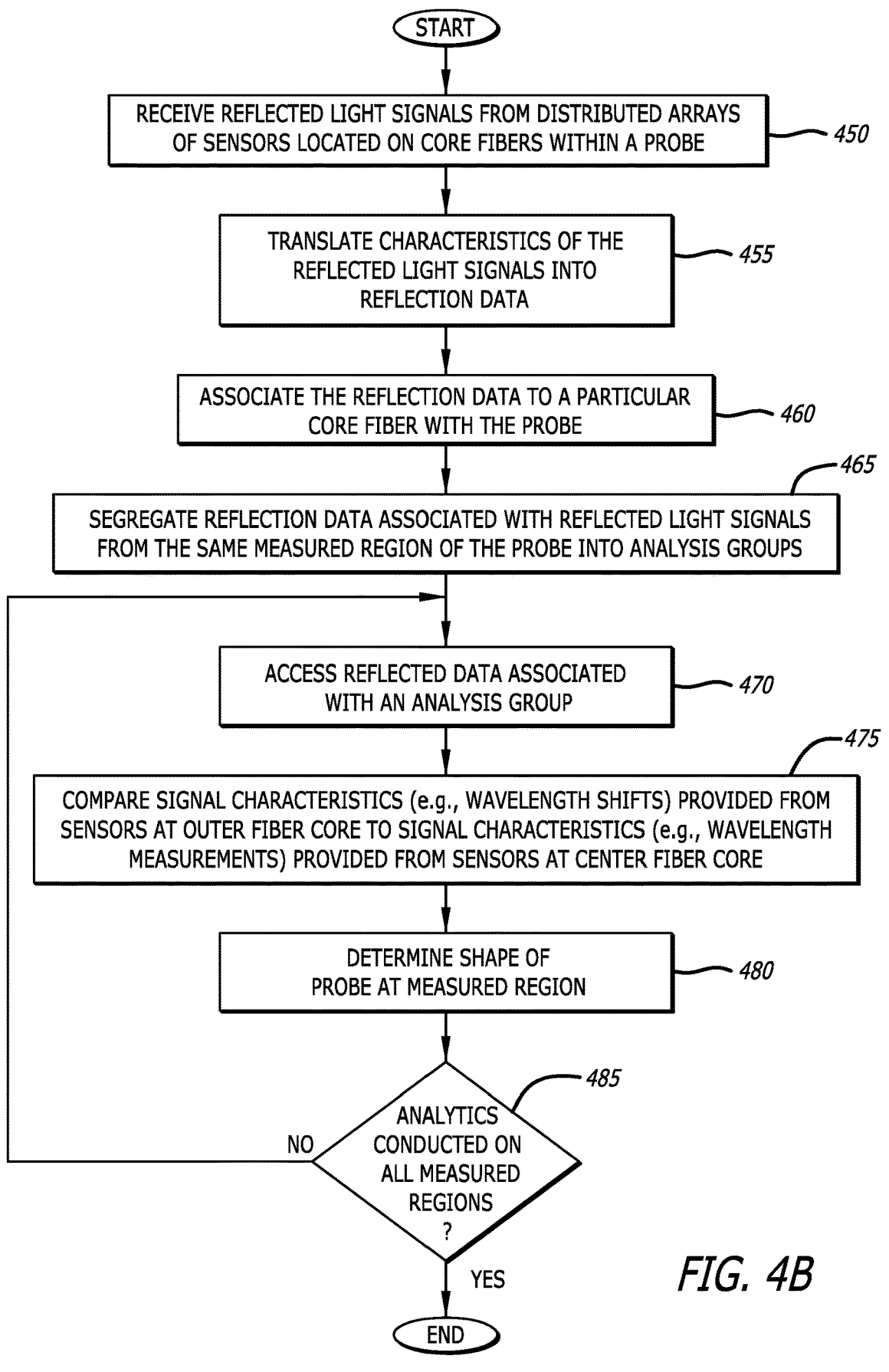

Referring to FIGS. 4A-4B, flowcharts of methods of operations conducted by the medical device system of FIG. 1 to achieve optic three-dimensional shape sensing are shown in accordance with some embodiments. The first micro-lumen is coaxial with the central axis of the probe. The first micro-lumen is configured to retain a center core fiber. Two or more micro-lumen, other than the first micro-lumen, are positioned at different locations circumferentially spaced along the circumferential edge of the probe. For example, two or more of the second plurality of micro-lumens may be positioned at different quadrants along the circumference edge of the probe.

Furthermore, each core fiber includes a plurality of sensors spatially distributed along its length between at least the proximal and distal ends of the probe. This array of sensors is distributed to position sensors at different regions of the core fiber to enable distributed measurements of strain throughout the entire length or a selected portion of the probe. These distributed measurements may be conveyed through reflected light of different spectral widths (e.g., specific wavelength or specific wavelength ranges) that undergoes certain wavelength shifts based on the type and degree of strain, including oscillations of the strain.

According to one embodiment of the disclosure, as shown in FIG. 4A, for each core fiber, broadband incident light is supplied to propagate through a particular core fiber (block 400). Unless discharged, upon the incident light reaching a sensor of a distributed array of sensors measuring strain on a particular core fiber, light of a prescribed spectral width associated with the first sensor is to be reflected back to an optical receiver within a console (blocks 405-410). Herein, the sensor alters characteristics of the reflected light signal to identify the type and degree of strain on the particular core fiber as measured by the first sensor (blocks 415-420). According to one embodiment of the disclosure, the alteration in characteristics of the reflected light signal may signify a change (shift) in the wavelength of the reflected light signal from the wavelength of the incident light signal associated with the prescribed spectral width. The sensor returns the reflected light signal over the core fiber and the remaining spectrum of the incident light continues propagation through the core fiber toward a distal end of the probe (blocks 425-430). The remaining spectrum of the incident light may encounter other sensors of the distributed array of sensors, where each of these sensors would operate as set forth in blocks 405-430 until the last sensor of the distributed array of sensors returns the reflected light signal associated with its assigned spectral width and the remaining spectrum is discharged as illumination.

Referring now to FIG. 4B, during operation, multiple reflected light signals are returned to the console from each of the plurality of core fibers residing within the corresponding plurality of micro-lumens formed within a probe. In particular, the optical receiver receives reflected light signals from the distributed arrays of sensors located on the center core fiber and the outer core fibers and translates the reflected light signals into reflection data, namely electrical signals representative of the reflected light signals including wavelength shifts caused by strain (blocks 450-455). The reflection data classification logic is configured to identify which core fibers pertain to which reflection data and segregate reflection data provided from reflected light signals pertaining to a particular measurement region (or similar spectral width) into analysis groups (block 460-465).

Each analysis group of reflection data is provided to sensing logic for analytics (block 470). Herein, the sensing logic compares wavelength shifts at each outer core fiber with the wavelength shift at the center core fiber positioned along central axis and operating as a neutral axis of bending (block 475). From this analytics, on all analytic groups (e.g., reflected light signals from sensors in all or most of the core fibers), the sensing logic may determine the shape the core fibers have taken in three-dimensional space, from which the sensing logic can determine the current physical state of the probe in three-dimensional space (blocks 480-485).

Figure 5:
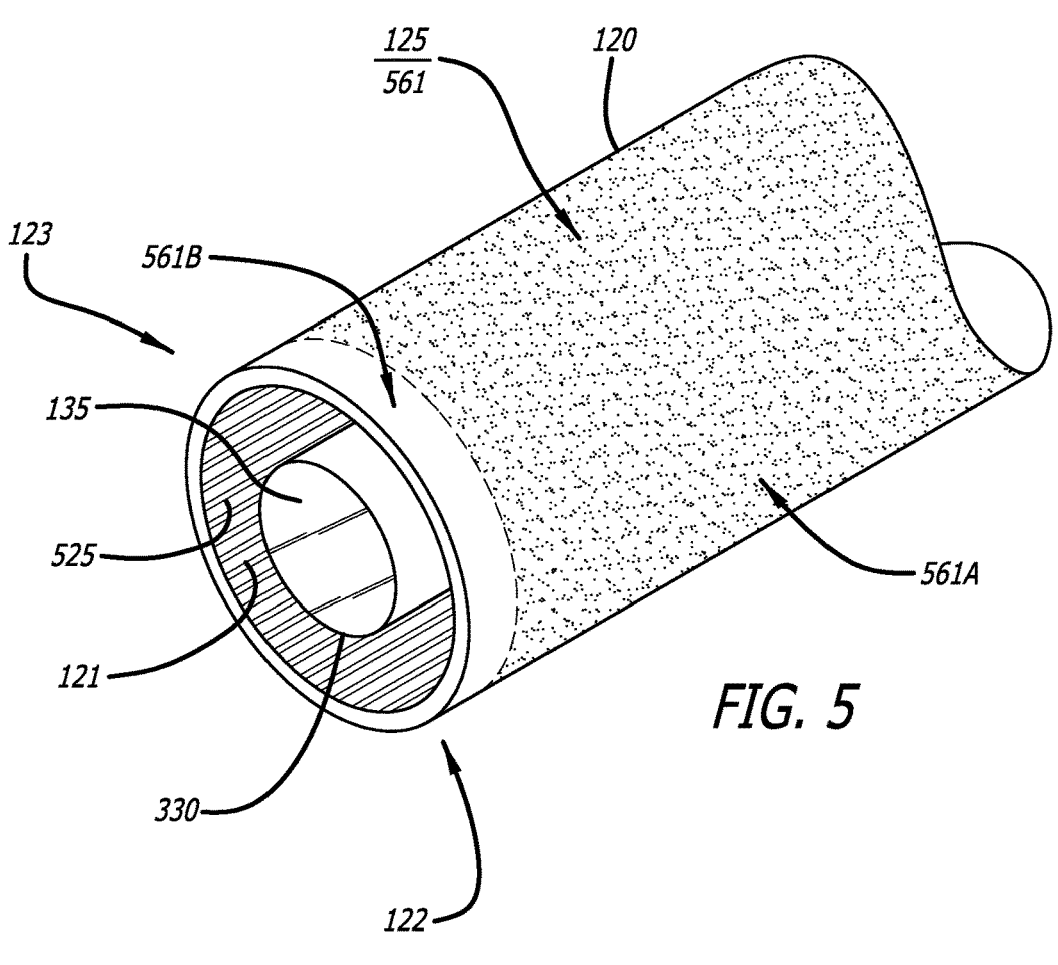
FIG. 5 is a detailed illustration of a distal portion of the elongate probe of FIG. 1, in accordance with some embodiments.

FIG. 5 illustrates a distal portion of the elongate probe 120. The elongate probe 120 includes the optical fiber 135 disposed within the lumen 121. The distal end 330 of the optical fiber 135 may be disposed adjacent the distal end 122 of the elongate probe 120. In some embodiments, the distal end 330 of the optical fiber 135 may be positioned substantially flush with the distal end 122.

The elongate probe 120 includes a cannula 561 defining the lumen 121. The cannula 561 is formed of an electrically conductive material to define the EC medium 125. The cannula 561 may be formed of a metallic material, such as stainless steel or Nitinol, for example. The cannula 561 extends to the distal end 122 of the probe 120 to define the conductive tip 123.

In some embodiments, the cannula 561 may include an electrically insulative coating 561A disposed on an outside surface and/or an inside surface of the cannula 561. In some embodiments, a distal end portion of the cannula 561B may be uncoated with the insulative coating 561A to define the conductive tip 123.

In the illustrated embodiments, the cannula 561 defines a distal open end of the lumen 121. In other embodiments, the cannula 561 may include a closed distal end. In some embodiments, the cannula 561 may include a welded or melted portion to the define the closed distal end.

In some embodiments, the cannula 561 may include an electrically conductive substance 525 disposed within the lumen 121. The electrically conductive substance 525 may extend uninterrupted from the proximal end 124 (see FIG. 1) to the distal end 122. Optionally, electrically conductive substance 525 may, alternatively or in addition to the cannula 561, define the EC medium 125 and/or the conductive tip 123. The electrically conductive substance 525 may include an electrically conductive epoxy.

FIGS. 6-13 illustrate further embodiments of the elongate probe depicting various implementations of the EC medium 125 and/or the conductive tip 123 that can, in certain respects, resemble components of the elongate probe 120 described in connection with FIGS. 1-5. It will be appreciated that all the illustrated embodiments may have analogous features. Relevant disclosure set forth above regarding similarly identified features thus may not be repeated hereafter. Moreover, specific features of the elongate probe 120 and related components shown in FIGS. 1-5 may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply equally to the features of the elongate probes of FIGS. 6-13. Any suitable combination of the features, and variations of the same, described with respect to the elongate probe 120 and components illustrated in FIGS. 1-6 can be employed with the elongate probes and components of FIGS. 6-13, and vice versa.

Figure 6:
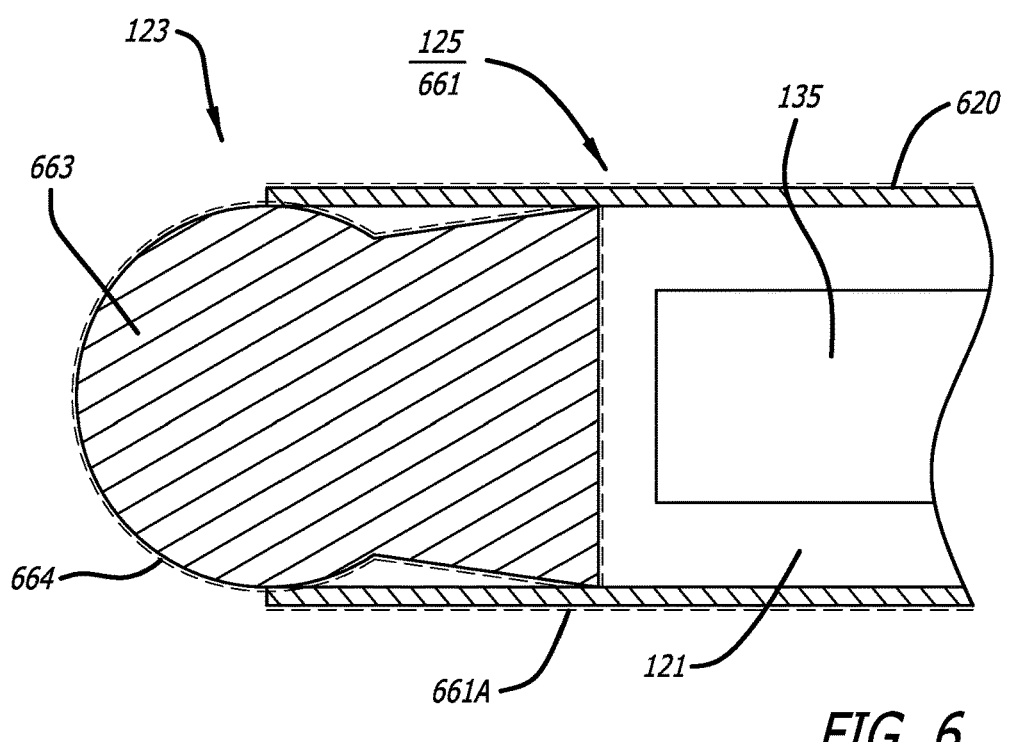
FIG. 6 is a detailed illustration of a distal portion of the elongate probe of FIG. 1 further including a conductive tip member, in accordance with some embodiments.

FIG. 6 illustrates a distal portion of the elongate probe 620. The elongate probe 620 includes the optical fiber 135 disposed within the lumen 121. The distal end 330 of the optical fiber 135 may be recessed proximally inward from the distal end 122 of the elongate probe 120.

The elongate probe 120 includes a cannula 661 defining the lumen 121. The cannula 661 is formed of an electrically conductive material to define the EC medium 125. The cannula 661 may be formed of a metallic material, such as stainless steel or Nitinol, for example. A conductive tip member 663 is electrically coupled with the cannula 661 to define the conductive tip 123. The conductive tip member 663 may be formed of an electrically conductive material, such as metal, a conductive epoxy, or a polymer infused with a conductive material. In some embodiments, the conductive tip member 663 may be composed of non-conductive material having a conductive coating 664 applied to the non-conductive material. A portion of the conductive tip member 663 may be disposed with the lumen 121, and as such, the cannula 661 may surround a portion of the conductive tip member 663. In some embodiments, the cannula 661 may include an electrically insulative coating 661A disposed on an outside surface and/or an inside surface of the cannula 661.

Figures 7, 8:
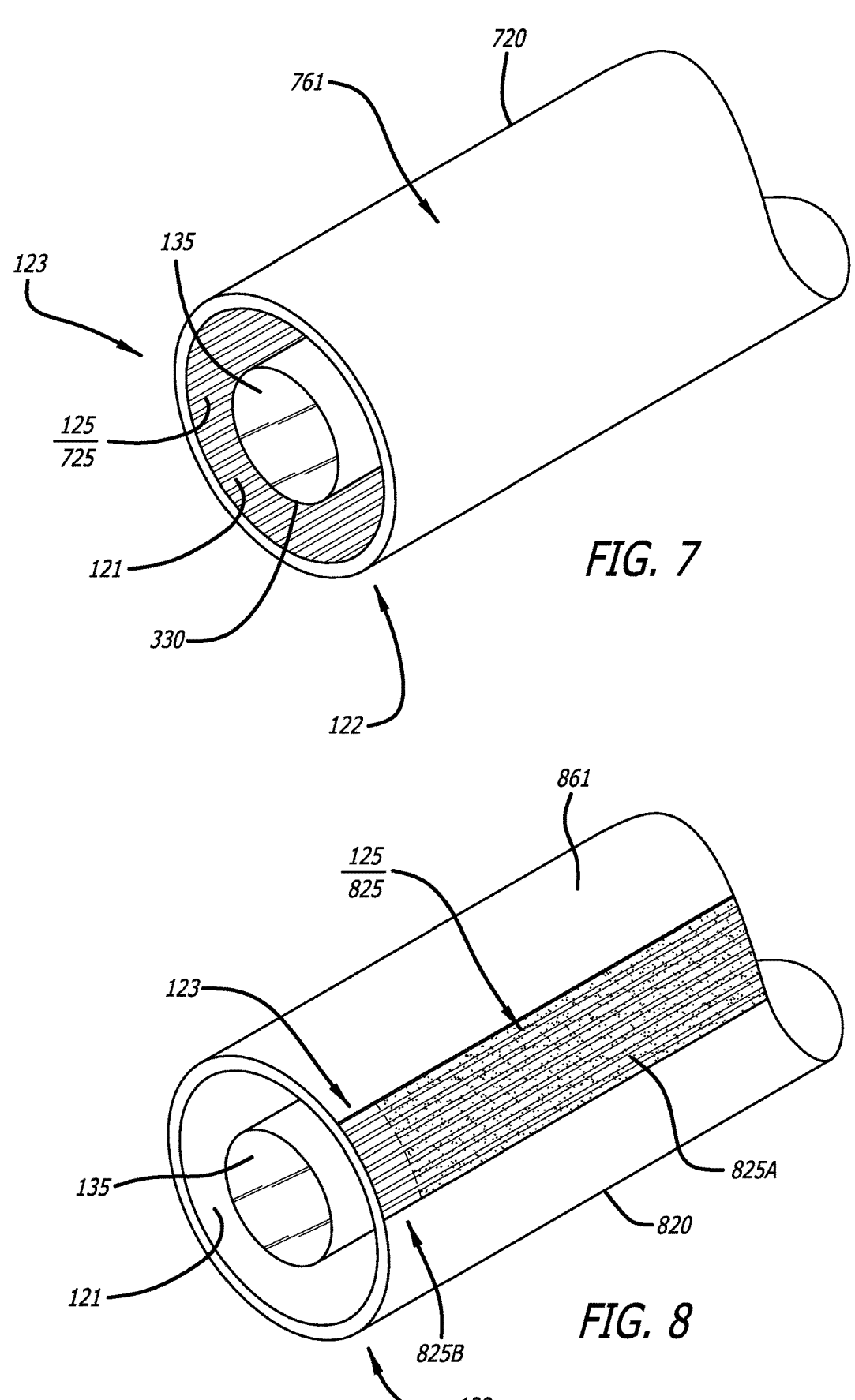
FIG. 7 is a detailed illustration of a distal portion of a second embodiment of the elongate probe, in accordance with some embodiments.
FIG. 8 is a detailed illustration of a distal portion of a third embodiment of the elongate probe, in accordance with some embodiments.

FIG. 7 illustrates a distal portion of the elongate probe 720. The elongate probe 720 includes the optical fiber 135 disposed within the lumen 121. The distal end 330 of the optical fiber 135 may be disposed adjacent the distal end 122 of the elongate probe 120. In some embodiments, the distal end 330 of the optical fiber 135 may be positioned substantially flush with the distal end 122.

The elongate probe 720 includes a cannula 761 defining the lumen 121. The cannula 761 is formed of an electrically non-conductive material (i.e., insulative). The cannula 761 may be formed of any suitable non-conductive material, such as a plastic material, for example. The elongate probe 720 further includes an electrically conductive substance 725 disposed within the lumen 121. The electrically conductive substance 725 extends uninterrupted from the proximal end (such as the proximal end 124 of FIG. 1) to the distal end 122 to define the EC medium 125. In the illustrated embodiment, the electrically conductive substance 725 is a saline solution filling the lumen 121. In other embodiments, the electrically conductive substance 725 may be any suitable ionic liquid. The electrically conductive substance 725 is exposed via an open distal end of the cannula 761 to define the conductive tip 123.

FIG. 8 illustrates a distal portion of the elongate probe 820. The elongate probe 820 includes the optical fiber 135 disposed within the lumen 121. The distal end 330 of the optical fiber 135 may be disposed adjacent the distal end 122 of the elongate probe 120. In some embodiments, the distal end 330 of the optical fiber 135 may be positioned substantially flush with the distal end 122.

The elongate probe 820 includes a cannula 861 defining the lumen 121. The cannula 861 is formed of an electrically non-conductive material (i.e., insulative). In the illustrated embodiment, the cannula 861 is formed of any suitable non-conductive material, such as a polymeric material, for example. In other embodiments, the cannula 861 may be formed of metallic material. The elongate probe 820 further includes a stripe (or trace) 825 of electrically conductive material disposed along an outside wall of the cannula 861. The stripe 825 extends uninterrupted from the proximal end (such as the proximal end 124 of FIG. 1) to the distal end 122 to define the EC medium 125. The stripe 825 of electrically conductive material may including a plating or a coating as may be applied via a painting or spraying process. The stripe 825 extends to the distal end 122 of the probe 820 to define the conductive tip 123. In some embodiments, the elongate probe 820 may include more than one stripe 825.

In some embodiments, the stripe 825 of electrically conductive material may include an electrically insulative coating 825A disposed on an outside surface of the stripe 825. In some embodiments, a distal end portion 825B of the stripe 825 may be uncoated with the insulative coating 825A to define the conductive tip 123.

Figure 9:
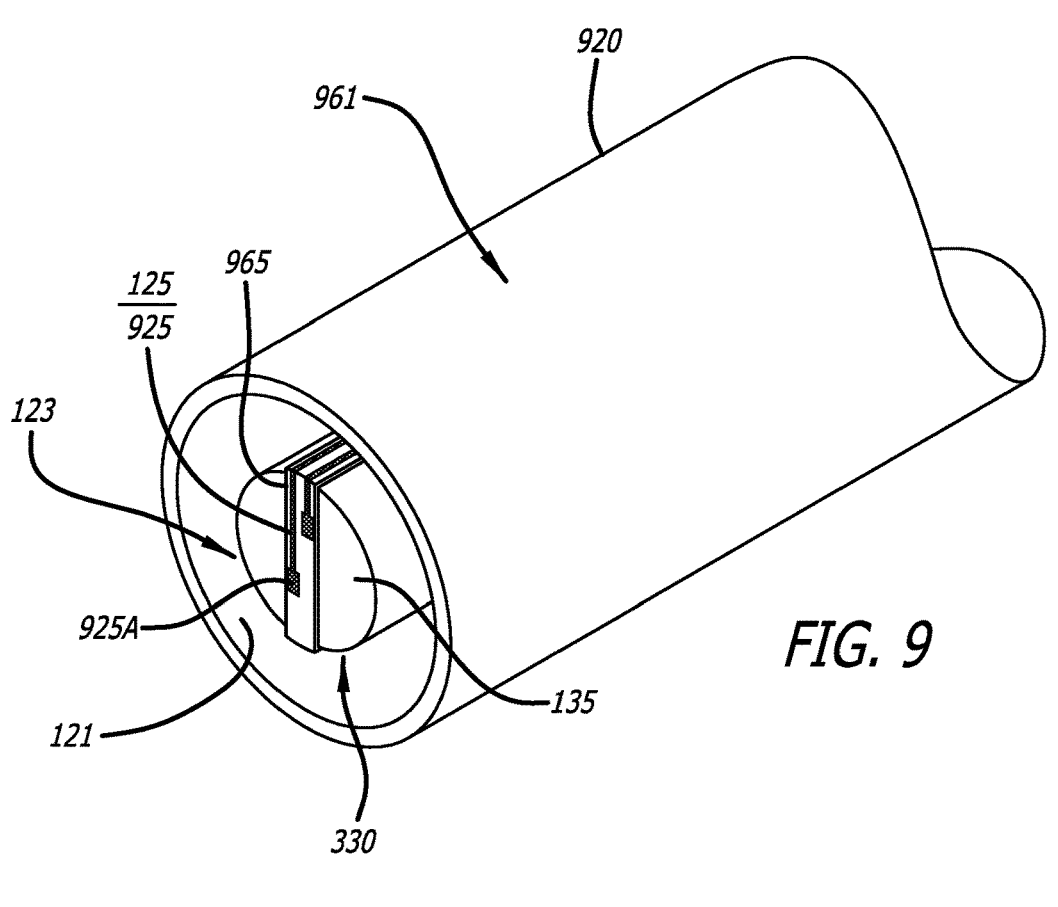
FIG. 9 is a detailed illustration of a distal portion of a fourth embodiment of the elongate probe, in accordance with some embodiments.

FIG. 9 illustrates a distal portion of the elongate probe 920. The elongate probe 920 includes the optical fiber 135 disposed within the lumen 121. The distal end 330 of the optical fiber 135 may be disposed adjacent the distal end 122 of the elongate probe 120. In some embodiments, the distal end 330 of the optical fiber 135 may be positioned substantially flush with the distal end 122.

The elongate probe 920 includes a cannula 961 defining the lumen 121. The cannula 961 may be formed of an electrically non-conductive material (i.e., insulative). The cannula 961 may be formed of any suitable non-conductive material, such as a plastic material, for example. The elongate probe 920 further includes a flex circuit 965 disposed within the lumen 121 together with the optical fiber 135. The flex circuit 965 may include a number (e.g., 1, 2, 3, or more) of traces extending uninterrupted from the proximal end (such as the proximal end 124 of FIG. 1) to the distal end 122 to define the EC medium 125. The flex circuit 965 extends to the distal end 122 of the probe 920 to define the conductive tip 123.

In some embodiments, the flex circuit 965 may include an exposed portion 925A of the number of traces adjacent the distal end 122 to define the conductive tip 123. In some embodiments, the flex circuit 965 may extend over the distal end 330 of the optical fiber 135. In some embodiments, the flex circuit 965 may be disposed within the lumen 121 along each of opposite sides of the optical fiber 135.

Figure 10:
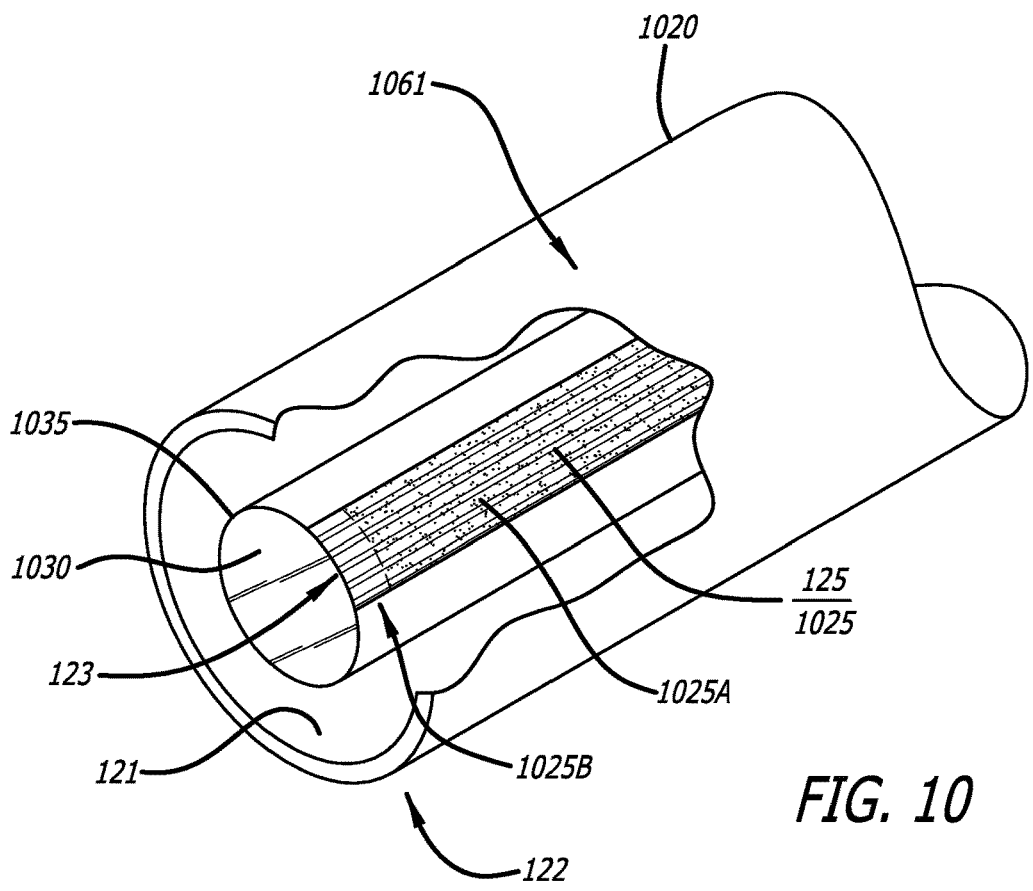
FIG. 10 is a detailed illustration of a distal portion of a fifth embodiment of the elongate probe, in accordance with some embodiments.

FIG. 10 illustrates a distal portion of the elongate probe 1020. The elongate probe 1020 includes the optical fiber 1035 disposed within the lumen 121. The optical fiber 1035 can, in certain respects, resemble components of the optical fiber 135 described in connection with FIGS. 1-3B. It will be appreciated that all the illustrated embodiments may have analogous features. Relevant disclosure set forth above regarding similarly identified features thus may not be repeated hereafter. Moreover, specific features of the optical fiber 1035 and related components shown in FIG. 10 may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply equally to the features of the optical fiber of FIG. 10. Any suitable combination of the features, and variations of the same, described with respect to the optical fiber 135 and components illustrated in FIGS. 1-3B can be employed with the optical fiber 1035 and components of FIG. 10, and vice versa.

The elongate probe 1020 includes a cannula 1061 defining the lumen 121. The cannula 1061 is formed of an electrically non-conductive material (i.e., insulative). The cannula 1061 may be formed of any suitable non-conductive material, such as a plastic material, for example. The distal end 1030 of the optical fiber 1035 may be disposed adjacent the distal end 122 of the elongate probe 1020. In some embodiments, the distal end 1030 of the optical fiber 1035 may be positioned substantially flush with the distal end 122.

The optical fiber 1035 includes a stripe (or trace) 1025 of electrically conductive material disposed along an outside wall of the optical fiber 1035. The stripe 1025 extends uninterrupted from the proximal end (such as the proximal end 124 of FIG. 1) of the elongate probe 1020 to the distal end 122 to define the EC medium 125. The stripe 1025 of electrically conductive material may including a plating or a coating as may be applied via a painting or spraying process. The stripe 1025 extends to the distal end 122 of the probe 1020 to define the conductive tip 123. In some embodiments, the elongate probe 1020 may include more than one stripe 1025.

In some embodiments, the stripe 1025 of electrically conductive material may include an electrically insulative coating 1025A disposed on an outside surface of the stripe 1025. In some embodiments, a distal end portion 1025B of the stripe 1025 may be uncoated with the insulative coating 1025A to define the conductive tip 123.

Figure 11:
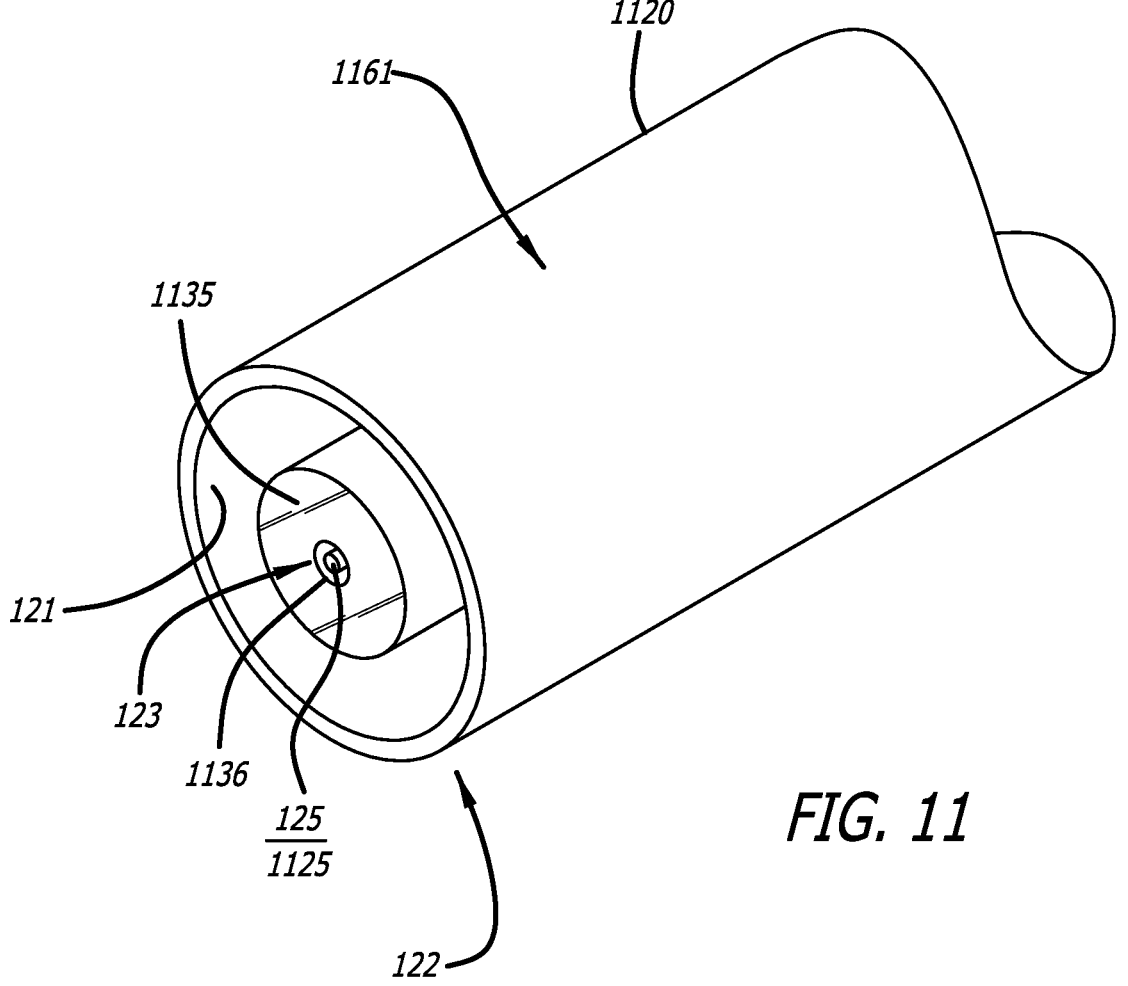
FIG. 11 is a detailed illustration of a distal portion of a sixth embodiment of the elongate probe, in accordance with some embodiments.

FIG. 11 illustrates a distal portion of the elongate probe 1120. The elongate probe 1120 includes the optical fiber 1135 disposed within the lumen 121. Similar to the optical fiber 1035 shown and described above, the optical fiber 1135 can, in certain respects, resemble components of the optical fiber 135 described in connection with FIGS. 1-3B.

The elongate probe 1120 includes a cannula 1161 defining the lumen 121. The cannula 1161 is formed of an electrically non-conductive material (i.e., insulative). The cannula 1161 may be formed of any suitable non-conductive material, such as a plastic material, for example. The distal end 1130 of the optical fiber 135 may be disposed adjacent the distal end 122 of the elongate probe 1120. In some embodiments, the distal end 1130 of the optical fiber 1135 may be positioned substantially flush with the distal end 122.

The optical fiber 1135 includes a wire 1125 embedded within the cladding 300 of the optical fiber 1135. The wire 1125 extends uninterrupted from the proximal end (such as the proximal end 124 of FIG. 1) of the elongate probe 1120 to the distal end 122 to define the EC medium 125. The wire 1125 may be disposed within a lumen 1136 of the optical fiber 1135. The wire 1125 extends to the distal end 122 of the probe 1120 to define the conductive tip 123. In some embodiments, the optical fiber 1135 may include more than one wire 1125.

Figures 12, 13:
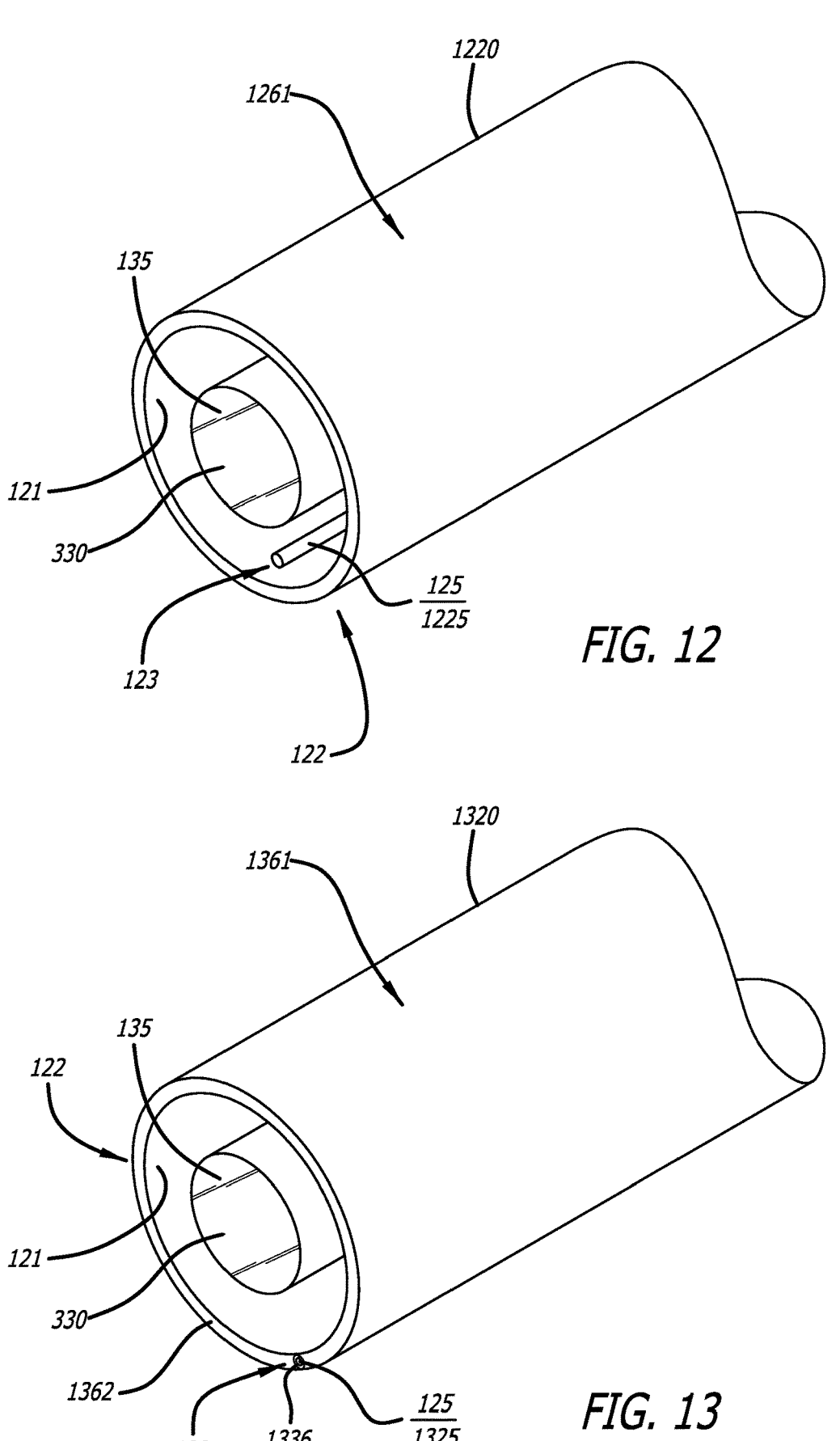
FIG. 12 is a detailed illustration of a distal portion of a seventh embodiment of the elongate probe, in accordance with some embodiments.
FIG. 13 is a detailed illustration of a distal portion of an eighth embodiment of the elongate probe, in accordance with some embodiments.

FIG. 12 illustrates a distal portion of the elongate probe 1220. The elongate probe 1220 includes the optical fiber 135 disposed within the lumen 121. The elongate probe 1220 includes a cannula 1261 defining the lumen 121. The cannula 1261 is formed of an electrically non-conductive material (i.e., insulative). The cannula 1261 may be formed of any suitable non-conductive material, such as a plastic material, for example. The distal end 330 of the optical fiber 135 may be disposed adjacent the distal end 122 of the elongate probe 1220. In some embodiments, the distal end 330 of the optical fiber 135 may be positioned substantially flush with the distal end 122.

The elongate probe 1220 includes a wire 1225 embedded extending along the elongate probe 1220. The wire 1225 extends uninterrupted from the proximal end (such as the proximal end 124 of FIG. 1) of the elongate probe 1220 to the distal end 122 to define the EC medium 125. In the illustrated embodiment, the wire 1225 is disposed within the lumen 121. In other embodiments, the wire 1225 may be disposed along an outside surface of the cannula 1261. The wire 1225 extends to the distal end 122 of the probe 1220 to define the conductive tip 123. In some embodiments, the optical fiber 135 may include more than one wire 1225.

FIG. 13 illustrates a distal portion of the elongate probe 1320. The elongate probe 1320 includes the optical fiber 135 disposed within the lumen 121. The elongate probe 1320 includes a cannula 1361 defining the lumen 121. The cannula 1361 is formed of an electrically non-conductive material (i.e., insulative). The cannula 1361 may be formed of any suitable non-conductive material, such as a plastic material, for example. The distal end 330 of the optical fiber 135 may be disposed adjacent the distal end 122 of the elongate probe 1320. In some embodiments, the distal end 330 of the optical fiber 135 may be positioned substantially flush with the distal end 122.

The optical fiber 1335 includes a wire 1325 embedded within the wall 1362 of the cannula 1361. The wire 1325 may be disposed within a lumen 1336. The wire 1325 extends uninterrupted from the proximal end (such as the proximal end 124 of FIG. 1) of the elongate probe 1320 to the distal end 122 to define the EC medium 125. The wire 1325 extends to the distal end 122 of the probe 1320 to define the conductive tip 123. In some embodiments, the optical fiber 135 may include more than one wire 1325.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. A medical device comprising:
an elongate probe configured for insertion into a patient body, the elongate probe defining a proximal end and a distal end;
an optical fiber extending along the elongate probe from the proximal end to the distal end; and
an electrically conductive (EC) medium extending along the elongate probe from the proximal end to a conductive tip at the distal end, wherein:
the EC medium is electrically connected to the conductive tip, and
during use of the medical device, electrical signals are transported along the EC medium.

2. The device of claim 1, wherein:
the elongate probe includes a cannula formed of a conductive material,
the cannula extends between the proximal end and the distal end,
the optical fiber is disposed within the cannula, and
the cannula defines the EC medium.

3. The device of claim 2, wherein:
the conductive tip includes a conductive tip member coupled with the cannula, and
the cannula surrounds at least a portion of the conductive tip member.

4. The device of claim 1, wherein:
the elongate probe includes a cannula formed of a non-conductive material, the cannula extending between the proximal end and the distal end;
the cannula defines a lumen extending along the cannula; and
the optical fiber is disposed with the lumen.

5. The device of claim 4, wherein:
the cannula includes a conductive substance disposed within the lumen, the conductive substance extending between the proximal end and the distal end; and
the conductive substance defines the EC medium.

6. The device of claim 5, wherein the conductive substance includes a saline solution.

7. The device of claim 4, wherein:
the cannula includes a flex circuit disposed within the lumen, the flex circuit including one or more traces extending between the proximal end and the distal end; and
the one or more traces define the EC medium.

8. The device of claim 4, wherein:
the cannula includes one or more wires extending along the cannula between the proximal end and the distal end; and
the one or more wires define the EC medium.

9. The device of claim 4, wherein:
the cannula includes one or more stripes of a conductive material disposed on an outside surface of the cannula, the one or more stripes extending between the proximal end and the distal end; and
the one or more stripes define the EC medium.

10. The device of claim 4, wherein:

the optical fiber includes one or more stripes of a conductive material disposed on an outside surface of the optical fiber, the one or more stripes extending between the proximal end and the distal end; and the one or more stripes define the EC medium.

11. The device of claim 1, wherein:

the optical fiber includes one or more core fibers extending along a longitudinal length of the optical fiber, each of the one or more core fibers including a plurality of sensors distributed along the longitudinal length and each sensor of the plurality of sensors being configured to (i) reflect a light signal of a different spectral width based on received incident light at the proximal end, and (ii) change a characteristic of the reflected light signal based on a condition experienced by the optical fiber.

12. The device of claim 1, wherein the optical fiber further includes:

one or more illuminating core fibers, each of the one or more illuminating core fibers configured to receive illuminating light at the proximal end and project the illuminating light away from the distal end, and one or more imaging core fibers, each of the one or more imaging core fibers configured to receive imaging light at the distal end and propagate the imaging light along the optical fiber from the distal end to the proximal end.

13. A medical system comprising:

a medical device comprising:

an elongate probe configured for insertion into a patient body, the elongate probe defining a proximal end and a distal end; and an optical fiber extending along the elongate probe from the proximal end to the distal end; and an electrically conductive (EC) medium extending along the elongate probe from the proximal end to a conductive tip at the distal end, wherein:

the EC medium is electrically connected to the conductive tip, and during use of the medical device, electrical signals are transported along the EC medium; and a console operatively coupled with the medical device at the proximal end, the console including one or more processors, and a non-transitory computer-readable medium having stored thereon logic that, when executed by the one or more processors, causes operations of the medical system that include:

providing an electrical signal to the patient body; and/or receiving the electrical signal from the patient body.

14. The system of claim 13, wherein:

the elongate probe includes a cannula formed of a conductive material, the cannula extends between the proximal end and the distal end, the optical fiber is disposed within the cannula, and the cannula defines the EC medium.

15. The system of claim 14, wherein:

the conductive tip includes a conductive tip member coupled with the cannula, and the cannula surrounds at least a portion of the conductive tip member.

16. The system of claim 13, wherein:

the elongate probe includes a cannula formed of a non-conductive material, the cannula extending between the proximal end and the distal end;

the cannula defines a lumen extending along the cannula; and the optical fiber is disposed with the lumen.

17. The system of claim 16, wherein:

the cannula includes a saline solution disposed within the lumen, the saline solution extending between the proximal end and the distal end; and the saline solution defines the EC medium.

18. The system of claim 16, wherein:

the cannula includes a flex circuit disposed within the lumen, the flex circuit including one or more traces extending between the proximal end and the distal end; and the one or more traces define the EC medium.

19. The system of claim 16, wherein:

the cannula includes one or more wires disposed within the lumen, the one or more wires extending between the proximal end and the distal end; and the one or more wires define the EC medium.

20. The system of claim 16, wherein:

the cannula includes one or more stripes of a conductive material disposed on an outside surface of the cannula, the one or more stripes extending between the proximal end and the distal end; and the one or more stripes define the EC medium.

21. The system of claim 16, wherein:

the optical fiber includes one or more stripes of a conductive material disposed on an outside surface of the optical fiber, the one or more stripes extending between the proximal end and the distal end; and the one or more stripes define the EC medium.

22. The system of claim 13, wherein:

the optical fiber includes one or more core fibers extending along a longitudinal length of the optical fiber, each of the one or more core fibers including a plurality of sensors distributed along the longitudinal length and each sensor of the plurality of sensors being configured to (i) reflect a light signal of a different spectral width based on received incident light at proximal end, and (ii) change a characteristic of the reflected light signal based on condition experienced by the optical fiber; and the operations further include determining a physical state of the elongate probe within the patient body, wherein determining the physical state includes:

providing an incident light signal to the optical fiber;

receiving reflected light signals of different spectral widths of the incident light signal by one or more of the plurality of sensors; and processing the reflected light signals associated with the one or more core fibers to determine the physical state.

* * * * *